United States Patent
Ford et al.

(10) Patent No.: US 11,260,056 B2
(45) Date of Patent: Mar. 1, 2022

(54) DIAMINOPYRIMIDINE P2X3 AND P2X2/3 RECEPTOR MODULATORS FOR USE IN THE TREATMENT OF COUGH

(71) Applicants: Afferent Pharmaceuticals, Inc., San Mateo, CA (US); Anthony P. Ford, Palo Alto, CA (US); Kathleen Sereda Glaub, San Leandro, CA (US); Michael M. Kitt, Mountain View, CA (US); Steven Smith, San Jose, CA (US)

(72) Inventors: Anthony P. Ford, Palo Alto, CA (US); Kathleen Sereda Glaub, San Leandro, CA (US); Michael M. Kitt, Mountain View, CA (US); Steven Smith, San Jose, CA (US)

(73) Assignee: AFFERENT PHARMACEUTICALS, INC., San Mateo, CA (US)

( * ) Notice: Subject to any disclaimer, the term of this patent is extended or adjusted under 35 U.S.C. 154(b) by 0 days.

(21) Appl. No.: 15/764,174

(22) PCT Filed: Sep. 23, 2016

(86) PCT No.: PCT/US2016/053223
§ 371 (c)(1),
(2) Date: Mar. 28, 2018

(87) PCT Pub. No.: WO2017/058645
PCT Pub. Date: Apr. 6, 2017

(65) Prior Publication Data
US 2018/0280388 A1    Oct. 4, 2018

Related U.S. Application Data

(60) Provisional application No. 62/336,381, filed on May 13, 2016, provisional application No. 62/234,584, filed on Sep. 29, 2015.

(51) Int. Cl.
| | | |
|---|---|---|
| *A61K 31/505* | (2006.01) | |
| *A61K 9/00* | (2006.01) | |
| *A61K 47/38* | (2006.01) | |
| *A61K 47/44* | (2017.01) | |
| *A61K 9/10* | (2006.01) | |
| *A61K 9/06* | (2006.01) | |
| *A61K 45/06* | (2006.01) | |
| *A61K 9/20* | (2006.01) | |
| *A61K 9/48* | (2006.01) | |

(52) U.S. Cl.
CPC .......... *A61K 31/505* (2013.01); *A61K 9/0014* (2013.01); *A61K 9/0053* (2013.01); *A61K 9/0078* (2013.01); *A61K 9/06* (2013.01); *A61K 9/10* (2013.01); *A61K 9/2054* (2013.01); *A61K 9/4858* (2013.01); *A61K 45/06* (2013.01); *A61K 47/38* (2013.01); *A61K 47/44* (2013.01)

(58) Field of Classification Search
CPC ...... A61K 31/505; A61K 45/06; A61K 47/38; A61K 47/44; A61K 9/0014; A61K 9/0053; A61K 9/0078; A61K 9/06; A61K 9/10; A61K 9/2054; A61K 9/4858; A61P 11/14; A61P 43/00
See application file for complete search history.

(56) References Cited

U.S. PATENT DOCUMENTS

| | | | |
|---|---|---|---|
| 7,531,547 B2 | 5/2009 | Dillon et al. | |
| 7,741,484 B2 | 6/2010 | Constantinescu et al. | |
| 7,799,796 B2 | 9/2010 | Dillon et al. | |
| 7,858,632 B2 | 12/2010 | Broka et al. | |
| 8,003,788 B2 | 8/2011 | Dvorak et al. | |
| 8,008,313 B2 * | 8/2011 | Broka .............. | A61K 31/506 514/275 |
| 2006/0029548 A1 | 2/2006 | Pelleg et al. | |
| 2008/0086004 A1 | 4/2008 | Dvorak et al. | |

(Continued)

FOREIGN PATENT DOCUMENTS

| | | |
|---|---|---|
| WO | 2007025925 A1 | 3/2007 |
| WO | 2008040652 A1 | 4/2008 |
| WO | 2015027212 A1 | 2/2015 |

OTHER PUBLICATIONS

Rayid et al. (European Respiratory Journal, 2013, https://erj.ersjournals.com/content/erj/42/Suppl_57/1965.full.pdf) (Year: 2013).*

(Continued)

*Primary Examiner* — Jean P Cornet
(74) *Attorney, Agent, or Firm* — Yong Zhao; Catherine D. Fitch

(57) ABSTRACT

Methods for treating cough, chronic cough and urges to cough associated with respiratory diseases with a P2X3 and/or a P2X2/3 receptor antagonist, the methods comprising administering to a subject in need thereof an effective amount of a compound of Formula (I):

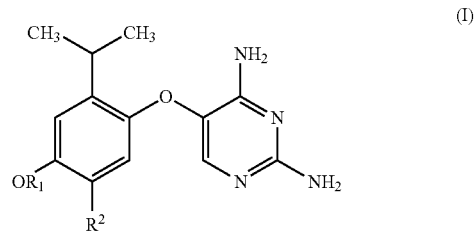

or a pharmaceutically acceptable salt thereof, wherein $R^1$ and $R^2$ are as defined herein.

11 Claims, 2 Drawing Sheets

(56) References Cited

U.S. PATENT DOCUMENTS

| | | | |
|---|---|---|---|
| 2008/0207655 A1* | 8/2008 | Dillon | C07D 239/48 514/272 |
| 2012/0122859 A1 | 5/2012 | Broka et al. | |
| 2015/0057299 A1* | 2/2015 | Ford | C07D 239/48 514/272 |

OTHER PUBLICATIONS https://www.thefreedictionary.com/treatment, accessed on Nov. 30, 2020. (Year: 2020).*
Morice et al., Eur Respir J Aug. 19, 2014; 44: 1132-1148 (Year: 2014).*
Morice et al., Thorax. Sep. 2006; 61(Suppl 1): i1-i24 (Year: 2006).*
Health.com, http://www.health.com/health/condition-article/00267700,00.html; Last updated: Apr. 1, 2009.
Belvisi, Maria G., Therapeutic advances for treatment-resistant cough, The Lancet 385, 2014, pp. 1160-1162.
"In pursuit of P2X3 antagonists: novel therapeutics for chronic pain and afferent sensitization", Purinergic Signalling, Kluwer Academic Publishers, DO, vol. 8, No. Suppl 11, Feb. 2012, pp. S3-S26, XP002699076, ISSN: 1573-9546, DOI: 10.1007/S11302-011-9271-6.
Peper, Abraham, Aspects of the Relationship Between Drug Dose and Drug Effect, International Dose-Response Society, 2009, 172-192, 7.
Abdulqawi, R. et al., P2X3 receptor antagonist (AF-219) in refractory chronic cough: a randomised, double-blind, placebo-controlled phase 2 study, Lancet, 2015, 1198-1205, 385.

\* cited by examiner

DIAMINOPYRIMIDINE P2X3 AND P2X2/3 RECEPTOR MODULATORS FOR USE IN THE TREATMENT OF COUGH

CROSS-REFERENCE TO RELATED APPLICATIONS

This application is a U.S. National Phase application under 35 U.S.C. § 371 of PCT Application No. PCT/US2016/053223, filed Sep. 23, 2016, which published as WO 2017/058645 A1 on Apr. 6, 2017, and claims priority from U.S. Patent Application No. 62/234,584, filed Sep. 29, 2015, and 62/336,381, filed May 13, 2016.

FIELD OF THE INVENTION

The present disclosure relates to methods for treatment of cough, chronic cough and urge to cough in respiratory conditions and disorders.

BACKGROUND OF THE INVENTION

The respiratory tract, or airways, participates in the vital process of gas exchange in order to support the demand for oxygen intake and carbon dioxide elimination. Vagal autonomic nerves control smooth muscles of the tracheobronchial tree, and thus caliber of airways, as well as liberation and movement of secretions (mucus and fluid). Control is coordinated within brainstem nuclei which regulate voluntary and autonomic outflow, relying on a rich input of vagal sensory signals from the airway tissues that in turn convey conscious sensation and trigger autonomic reflexes. Vagal sensory fibers arise mostly from cell bodies within jugular and nodose ganglia, and their activity is regulated by a range of chemical substances (Carr & Undem (2003) Respirology 8(3):291-301). One such substance is ATP, which sensitizes vagal afferents and serves as a convergent mechanosensory airways signal (Weigand, Ford and Undem (2012) J Physiol. 590(16):4109-20).

ATP activates purinoceptors (e.g., P2X3 and P2X2/3), which mediate many physiological and pathological roles (See, Burnstock (1993) Drug Dev. Res. 28:195-206). ATP stimulates and sensitizes sensory nerve endings resulting in intense sensations such as pain, discomfort, urgency, itch and urge and a pronounced increase in sensory nerve discharge, largely via P2X3 receptor activation on afferent nerve fibers innervating rodent and human tissues and organs, especially the hollow viscera.

Data suggest that ATP may be released from epithelial and interstitial cells of hollow organs (such as airways, bladder) as a result of distention, movement, pressure or inflammation (Burnstock (1999) J. Anatomy 194:335-342; and Ferguson et al. (1997) J. Physiol. 505:503-511). ATP thus serves a role in conveying information to sensory neurons located in epithelial and subepithelial compartments, e.g., subepithelial lamina propria (Namasivayam, et al. (1999) BJU Intl. 84:854-860; Weigand, Ford and Undem (2012) J Physiol. 590(16):4109-20).

Undem and co-workers have reported that P2X3 and P2X2/3 receptors are widely expressed and modulate function of nodose and jugular afferent fibers in mammalian airways (Weigand, Ford and Undem (2012) J Physiol. 590 (16):4109-20). Additionally, in a guinea pig model of ATP or histamine potentiation of citric acid induced cough, P2X subfamily receptors were implicated although contribution of P2X3 or P2X2/3 receptors was not deduced (Kamei, Takahashi, Yoshikawa, Saitoh (2005) Eur J Pharmacol. 528(158-161); Kamei and Takahashi. (2006) Eur J Pharmacol. 547:160-164). Finally, it has been shown in human studies that patients with airway disease associated with cough and breathlessness (such as asthma, COPD or pulmonary fibrosis) have excess ATP concentrations in their airway fluids (Esther, Alexis and Picher. (2011) Subcell. Biochem. 55:75-93; Lommatzsch et al. (2010) Am J Respir Crit Care Med. 181(9):928-34), and that the inhalation by asthmatic patients of nebulized ATP is able to activate airways sensations leading to urge to cough and precipitating cough itself (Pellegrino et al. (1996) J Appl Physiol. 81(2):964-75; Basoglu et al. (2005) Chest. 128(4):1905-9), although the site of action of this effect of ATP, and receptor(s) involved have not been elucidated.

There is accordingly a need for methods of treating diseases, conditions and disorders mediated by P2X3 and/or P2X2/3 receptors, as well as a need for compounds that act as modulators of P2X receptors, including antagonists of P2X3 and P2X2/3 receptors. Such diseases and disorders are herein shown to include cough, chronic cough and urge to cough, including cough associated with a respiratory disease or disorder. Chronic cough is distressing and functionally disabling, and no novel licensed treatments for cough have appeared in approximately 50 years.

SUMMARY OF THE INVENTION

The present disclosure provides methods for treating cough-impacted respiratory diseases using a P2X3 and/or a dual P2X3-P2X2/3 receptor antagonist. More specifically, respiratory diseases can include acute or sub-acute cough, urge to cough, and chronic cough. These respiratory diseases can be largely corrected by antagonism of P2X3-containing receptors (e.g., P2X3 and P2X2/3). Moreover, the compounds exemplified herein (e.g., diaminopyrimidine P2X3/P2X2/3 antagonists) are highly effective at attenuating the cough-related symptoms of many respiratory diseases including acute and sub-acute cough, urge to cough, and chronic cough.

Accordingly, in one aspect, the present disclosure is directed to a method for treating a subject for cough or urge to cough associated with a respiratory disease. The method can comprise administering to the subject in need thereof an effective amount of a compound of Formula (I):

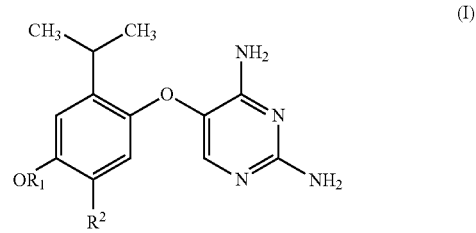

or a pharmaceutically acceptable salt thereof.

In one or more embodiments, $R^1$ is hydrogen or optionally substituted $C_1$-$C_6$ alkyl. In one or more embodiments, $R^2$ is: alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

In one or more embodiments, the respiratory symptom, condition or disorder is attenuated by a P2X3 or P2X3-

P2X2/3 receptor antagonist. The respiratory disease can be selected from many conditions where cough hypersensitivity prevails, and may include unexplained cough or cough associated with upper respiratory infection, chronic obstructive pulmonary disease (COPD), asthma, idiopathic pulmonary fibrosis, and the like.

In one or more embodiments, the cough is sub-acute or chronic cough, treatment-resistant cough, idiopathic chronic cough, post-viral cough, iatrogenic cough, cough associated with post-nasal drip, cough associated with upper respiratory infection, asthma and/or COPD, cough associated with interstitial disease, cough associated with gastro esophageal reflux disease (GERD) and/or cough associated with smoking or a form of bronchitis. The iatrogenic cough can be induced by an ACE-inhibitor. Additionally, the interstitial disease can be pulmonary fibrosis.

In another aspect, the present disclosure is directed to a method for treating chronic cough in a patient in need thereof. The method can comprise administering an effective amount of a compound of Formula (I):

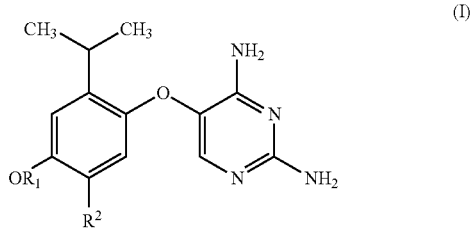

(I)

or a pharmaceutically acceptable salt thereof.

In one or more embodiments, $R^1$ is hydrogen or optionally substituted $C_1$-$C_6$ alkyl. In one or more embodiments, $R^2$ is: alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

In one or more embodiments, the chronic cough is idiopathic or treatment resistant cough. The cough can be daytime cough.

In another aspect, the present disclosure provides a method for treating neuronal hypersensitivity underlying acute, sub-acute or chronic cough. The method comprises administering an effective amount of a compound of Formula (I):

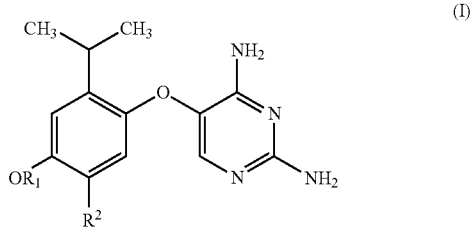

(I)

or a pharmaceutically acceptable salt thereof.

In one or more embodiments, $R^1$ is hydrogen or optionally substituted $C_1$-$C_6$ alkyl. In one or more embodiments, $R^2$ is: alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

In one or more embodiments, the chronic cough is idiopathic or treatment resistant cough. The cough can be daytime cough.

In some embodiments of any of the above aspects, $R^1$ can be methyl or hydrogen. In some embodiments of any of the above aspects, $R^2$ can be haloalkyl, aminosulfonyl, alkylsulfonyl alkylcarbonyl or carboxyalkyl. In some embodiments, $R^2$ is haloalkyl, further wherein the alkyl is methyl. $R^2$ can also be aminosulfonyl, carboxyalkyl, or alkylcarbonyl.

In one or more embodiments, of any of the above aspects, no greater than about 500 mg of the compound of Formula (I) is administered once or twice daily. The compound of Formula (I) can be administered for days, weeks, months or years, including indefinitely. For instance, the compound of Formula (I) is administered for days, weeks, months or years, including indefinitely at no greater than about 1 mg once or twice daily; at no greater than about 2.5 mg once or twice daily; at no greater than about 5 mg once or twice daily, at no greater than about 7.5 mg once or twice daily, at no greater than about 10 mg once or twice daily, at no greater than about 15 mg once or twice daily, at no greater than about 20 mg once or twice daily, at no greater than about 25 mg once or twice daily, at no greater than about 30 mg once or twice daily, at no greater than about 40 mg once or twice daily, at no greater than about 50 mg once or twice daily, at no greater than about 100 mg once or twice daily, at no greater than about 150 mg once or twice daily, at no greater than about 200 mg once or twice daily, at no greater than about 300 mg once or twice daily, at no greater than about 400 mg once or twice daily.

In one or more embodiments, of any of the above aspects, at least about 1 mg of the compound of Formula (I) is administered once or twice daily. The compound of Formula (I) can be administered for days, weeks, months or years, including indefinitely. For instance, at least about 2.5 mg of the compound of Formula (I) may be administered for days, weeks, months or years, including indefinitely once or twice daily; at least about 5 mg of the compound of Formula (I) may be administered once or twice daily; at least about 7.5 mg of the compound of Formula (I) may be administered once or twice daily, at least about 10 mg of the compound of Formula (I) may be administered once or twice daily, at least about 15 mg of the compound of Formula (I) may be administered once or twice daily, at least about 20 mg of the compound of Formula (I) may be administered once or twice daily, at least about 25 mg of the compound of Formula (I) may be administered once or twice daily, at least about 30 mg of the compound of Formula (I) may be administered once or twice daily, at least about 40 mg of the compound of Formula (I) may be administered once or twice daily, at least about 50 mg of the compound of Formula (I) may be administered once or twice daily, at least about 100 mg of the compound of Formula (I) may be administered once or twice daily, at least about 150 mg of the compound of Formula (I) may be administered once or twice daily, at least about 200 mg of the compound of Formula (I) may be administered once or twice daily, at least about 300 mg of the compound of Formula (I) may be administered once or twice daily, at least about 400 mg of the compound of Formula (I) may be administered once or twice daily.

In one or more embodiments, of any of the above aspects, the dose of the compound of Formula (I) is administered once or twice daily in an amount, and pursuant to a dosing regimen sufficient to achieve a desired target concentration of the compound of Formula (I) in plasma. The compound of Formula (I) can be administered for days, weeks, months or years, including indefinitely. For instance, the dose of the compound of Formula (I) may be administered for days, weeks, months or years, including indefinitely in an amount, and pursuant to a dosing regimen sufficient to achieve an average plasma concentration of 20-200 ng/mL; in some embodiments, the dose of the compound of Formula (I) is administered in an amount, and pursuant to a dosing regimen sufficient to achieve an average plasma concentration of 20-100 ng/mL; in some embodiments, the dose of the compound of Formula (I) is administered in an amount, and pursuant to a dosing regimen sufficient to achieve an average plasma concentration of 20-50 ng/mL; in some embodiments, the dose of the compound of Formula (I) is administered in an amount, and pursuant to a dosing regimen sufficient to achieve an average plasma concentration of 50-200 ng/mL; in some embodiments, the dose of the compound of Formula (I) is administered in an amount, and pursuant to a dosing regimen sufficient to achieve an average plasma concentration of 50-100 ng/mL; in some embodiments, the dose of the compound of Formula (I) is administered in an amount, and pursuant to a dosing regimen sufficient to achieve an average plasma concentration of 100-200 ng/mL.

In one or more embodiments, of any of the above aspects, the dose of the compound of Formula (I) is administered once or twice daily in an amount, and pursuant to a dosing regimen sufficient to achieve a desired $C_{max}/C_{min}$ ratio (i.e., the ratio between the maximum concentration ($C_{max}$) of the compound of Formula (I) in plasma between the dosing intervals and the minimum concentration ($C_{min}$) of the compound of Formula (I) in plasma between the dosing intervals). The compound of Formula (I) can be administered for days, weeks, months or years, including indefinitely. For instance, the dose of the compound of Formula (I) may be administered for days, weeks, months or years, including indefinitely in an amount, and pursuant to a dosing regimen sufficient to achieve a $C_{max}/C_{min}$ ratio between 1 and 5; in some embodiments, the dose of the compound of Formula (I) is administered in an amount, and pursuant to a dosing regimen sufficient to achieve a $C_{max}/C_{min}$ ratio between 1 and 2; in some embodiments, the dose of the compound of Formula (I) is administered in an amount, and pursuant to a dosing regimen sufficient to achieve a $C_{max}/C_{min}$ ratio between 1 and 3; in some embodiments, the dose of the compound of Formula (I) is administered in an amount, and pursuant to a dosing regimen sufficient to achieve a $C_{max}/C_{min}$ ratio between 1 and 4; in some embodiments, in some embodiments, the dose of the compound of Formula (I) is administered in an amount, and pursuant to a dosing regimen sufficient to achieve a $C_{max}/C_{min}$ ratio between 2 and 4; in some embodiments, the dose of the compound of Formula (I) is administered in an amount, and pursuant to a dosing regimen sufficient to achieve a $C_{max}/C_{min}$ ratio between 2 and 3; in some embodiments, the dose of the compound of Formula (I) is administered in an amount, and pursuant to a dosing regimen sufficient to achieve a $C_{max}/C_{min}$ ratio between 3 and 5; in some embodiments, the dose of the compound of Formula (I) is administered in an amount, and pursuant to a dosing regimen sufficient to achieve a $C_{max}/C_{min}$ ratio between 4 and 5.

In one or more embodiments of any of the above aspects, the chronic cough is refractory chronic cough. In one or more embodiments, of any of the above aspects, the chronic cough is reduced by about 50-90% (e.g., about 55%, 60%, 65%, 70%, 75%, 80%, or 85%).

In one or more embodiments of any of the above aspects, the P2X3 or P2X2/3 antagonist compound is selected from Compounds 1-38. For instance, the compound can be selected from Compounds 6, 7, 13, 16, 20, 27, 34 and 37 (e.g., the compound can be Compound 16).

In one or more embodiments, the present disclosure relates to a method for treating the symptoms of cough and urge to cough associated with a respiratory disease by administering a compound of Formula (I). For example, the present disclosure relates to a method of treatment of the symptoms of chronic cough and/or urge to cough associated with a respiratory disease or disorder mediated by a P2X3 or P2X2/3 receptor antagonist by administering a compound of Formula (I).

In one or more embodiments, the present disclosure relates to methods for reducing daytime chronic cough in idiopathic/treatment-resistant chronic cough. The present disclosure also relates to a method of treating neuronal hypersensitivity underlying chronic cough.

In one or more embodiments, the methods of the present disclosure relate to treating, preventing or ameliorating the respiratory diseases and disorders described herein, or symptoms thereof, described herein in a patient in need thereof by administering a compound selected from Compounds 1-39. For example, the compound is selected from Compounds 6, 7, 13, 17, 21, 28, 35 and 38. For example, the compound is Compound 16.

The present disclosure also provides pharmaceutical compositions of the compounds described herein and methods of preparing the same.

As set forth in the Detailed Description below, the present disclosure features a class of P2X3 and P2X2/3 antagonists for treating or alleviating cough and urge to cough, including chronic cough. The present disclosure has the advantage of addressing the root cause driving cough hypersensitivity in these illnesses instead of merely suppressing central modulation of the symptom perception. For instance, the present disclosure offers methods to reduce the activity of afferent nerves that ultimately trigger the persistent and inappropriate urge to cough in a sensitized subject (e.g., a human). The present disclosure also has the advantage of giving highly selective P2X3 and P2X2/3 antagonists. Further features and advantages are set forth in the Detailed Description below and will be apparent to one of skill in the art.

DETAILED DESCRIPTION OF THE INVENTION

Definitions

Figure 1:
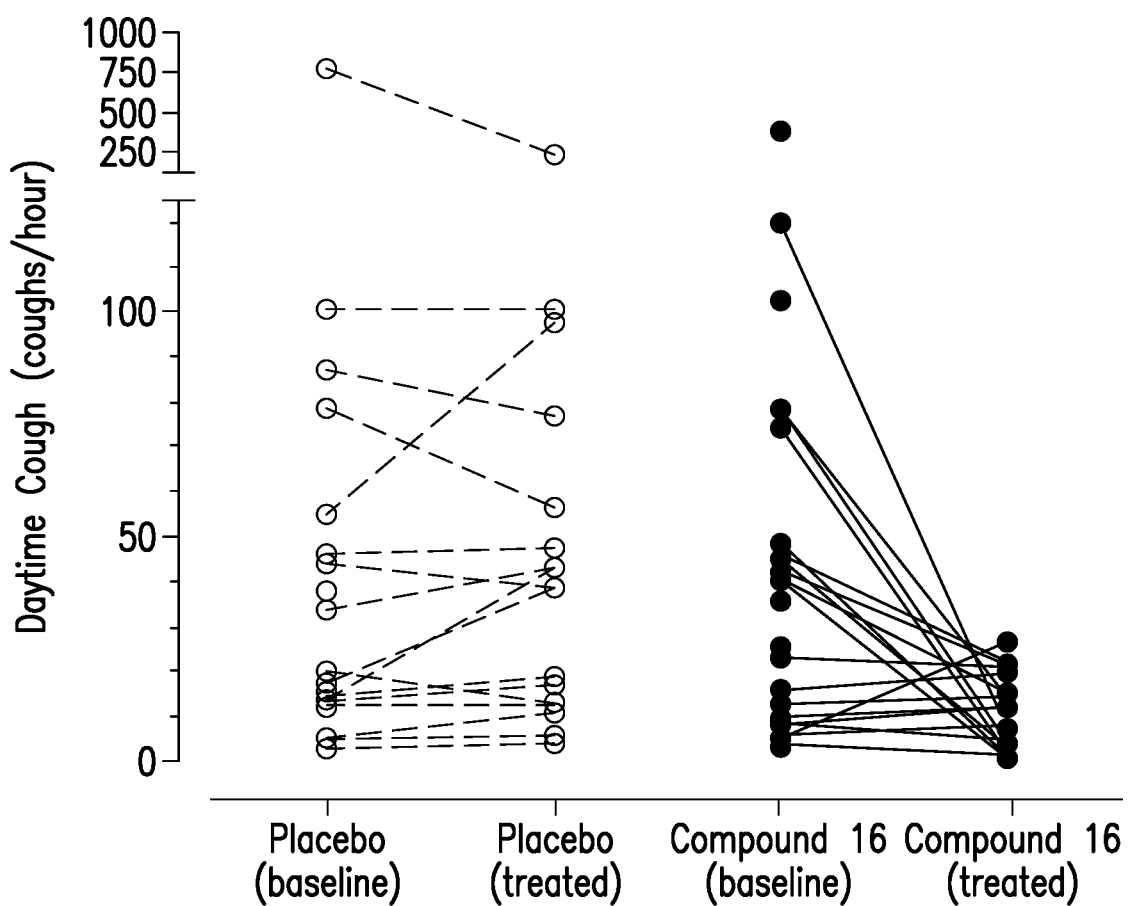
FIG. 1 is a graph depicting the effect of Compound 16 on objectively recorded daytime cough frequency (coughs per hour) in treatment-resistant chronic cough patients.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

As used herein in connection with numerical values, the terms "approximately" and "about" mean+/−10% of the indicated value, including the indicated value.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is (C=O) and R" is alkyl as defined herein.

"Alkylsulfonyl" means a moiety of the formula —R'—R", where R' is —SO$_2$— and R" is alkyl as defined herein.

"Alkylsulfonylalkyl" means a moiety of the formula —R'—R"—R'" where R' is alkylene, R" is —SO$_2$— and R'" is alkyl as defined herein.

"Alkylamino" means a moiety of the formula —NR—R' wherein R is hydrogen or alkyl and R' is alkyl as defined herein.

"Alkylsulfanyl" means a moiety of the formula —SR wherein R is alkyl as defined herein.

"Amino" means a moiety of the formula —NHR wherein R can be hydrogen or alkyl.

"Amido" means a moiety of the formula —NR(CO)R'— wherein R and R' can be H or alkyl as defined herein.

"Hydroxy" means a moiety of the formula —OH.

"Haloalkoxy" means a group of the formula —OR, wherein R is a haloalkyl group as defined herein.

"Nitro" means a group of the formula —NO$_2$. "Alkylcarbonyl" refers to a group of the formula —(CO)R wherein R is an alkyl group as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminosulfonyl" means a group —SO$_2$—NRR' wherein R and R' each independently is hydrogen or alkyl as defined herein.

"Alkylsulfonylamido" means a moiety of the formula —NR'SO$_2$—R wherein R is alkyl and R' is hydrogen or alkyl.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylsulfonyl" means a group of the formula —SO$_2$—R wherein R is aryl as defined herein.

"Antagonist" refers to a compound that diminishes or prevents the action of another compound or receptor site.

"Cyanoalkyl"" means a moiety of the formula —R'—R", where R' is alkylene as defined herein and R" is cyano or nitrile.

The terms "halo", "halogen" and "halide", which may be used interchangeably, refer to a substituent fluoro, chloro, bromo, or iodo.

"Haloalkyl" means alkyl as defined herein in which one or more hydrogen atoms have been replaced with the same or different halogen. Exemplary haloalkyls include —CH$_2$Cl, —CH$_2$CF$_3$, —CH$_2$CCl$_3$, perfluoroalkyl (e.g., —CF$_3$), and the like.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1- hydroxymethylethyl, 2,3-dihydroxybutyl, 3,4-dihydroxybutyl and 2-(hydroxymethyl)-3-hydroxypropyl "Carboxy" means a group of the formula —O—C(O)—OH.

"Sulfonamido" means a group of the formula —SO$_2$—NR'R" wherein R' and R" each independently is hydrogen or alkyl.

"Optionally substituted", for example when used with the term alkyl, means an alkyl group which is optionally substituted independently with one to three substituents, preferably one or two substituents selected from any of the substituents defined herein, for instance alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present disclosure are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes described herein rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvate" or "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as H$_2$O, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Cough related respiratory disorder" or "respiratory disease" refers to, without limitation, cough hypersensitivity syndrome, chronic obstructive pulmonary disease (COPD), asthma, bronchospasm, and the like. Respiratory disorders include, for example, sub-acute or chronic cough, treatment-resistant cough, idiopathic chronic cough, cough associated with upper respiratory infection, post-viral cough, iatrogenic cough (e.g., as induced by ACE-inhibitors), idiopathic pulmonary fibrosis or cough associated with smoking or a form of bronchitis. Respiratory disorders can include urge to cough associated with any respiratory disease, for example urge to cough associated with chronic obstructive pulmonary disease (COPD), cough-variant asthma, interstitial lung disease, or whooping cough.

"Acute cough" is understood to mean a cough lasting up to two weeks in duration. For instance, acute cough can be the result of an acute disease, such as a cold or flu. An acute cough will disappear when the underlying cause (e.g., cold or flu) is eliminated.

"Sub-acute cough" is understood to mean a cough lasting between two and eight weeks. In some cases, a sub-acute cough follows a period in which a subject is infected with a disease (e.g., cold or flu). A sub-acute cough is one that often remains after the underlying cause has been removed. For instance, a sub-acute cough is found post-infection (e.g., post-viral infection).

"Chronic cough" refers to a persistent or refractory cough lasting longer than eight weeks that may not have an obvious underlying cause and may not be associated with other respiratory diseases, such as asthma or COPD (i.e., idiopathic). Chronic cough is also characterized in that there are no hallmarks to define and diagnose it, in contrast to other respiratory diseases (e.g., COPD). Another characteristic of chronic cough is that a subject suffering from chronic cough may be apparently normal in most other respects. Chronic cough is characterized by frequent coughing (e.g., at least 5-10 coughs per hour during daytime), and bothersome coughing during sleep. Chronic cough can last for a period of years, including over a decade.

In order to determine if a subject is afflicted by a chronic cough, a practitioner or clinician can perform a three-step test. First, the subject can be treated for putative post-nasal drips. In some cases, such treatment takes the form of an antihistamine. Second, the subject can be treated with a proton-pump inhibitor (e.g., to treat putative gastro-esophageal disease such as reflux disease). Third, a subject can be treated with steroids (e.g., to treat a putative case of asthma).

If a subject continues to display a chronic cough after the above three-step treatment regimen, the cough is said to be chronic cough and is likely refractory. It is understood that patients suffering from refractory cough often have suffered both acute and sub-acute cough before being diagnosed with chronic cough.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes: inhibiting the disease state, i.e., arresting the development of the disease state or its clinical symptoms, or relieving the disease state, i.e., causing temporary or permanent regression of the disease state or its clinical symptoms.

"Preventing" or "prevention" of a disease state includes causing the clinical symptoms of the disease state not to develop in a subject that may be exposed to or predisposed to the disease state, but does not yet experience or display symptoms of the disease state. For example, treating or preventing a respiratory disease or disorder includes treating or preventing the symptoms the disorder such as cough and/or urge to cough associated with a respiratory disease.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0; a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

All patents and publications identified herein are incorporated herein by reference in their entirety.

Methods

The present disclosure provides compounds and methods for treating a respiratory disease mediated by a P2X3 or P2X2/3 receptor antagonist, said method comprising administering to a subject in need thereof an effective amount of a compound of Formula (I):

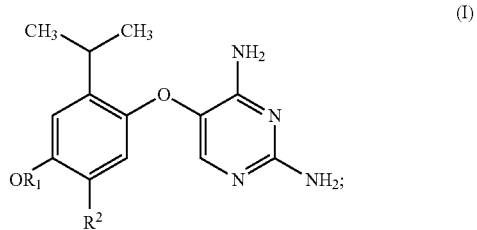

wherein:

$R^1$ is hydrogen or optionally substituted $C_1$-$C_6$ alkyl;

$R^2$ is: alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

Exemplary respiratory diseases treatable with the compounds and methods of the present disclosure include acute, sub-acute or chronic cough, treatment-resistant cough, idiopathic chronic cough, post-viral cough, whooping cough, iatrogenic cough (e.g., as induced by ACE-inhibitors), idiopathic pulmonary fibrosis or cough associated with smoking or a form of bronchitis. A disease treatable by the methods described herein includes urge to cough associated with any respiratory disease, for example urge to cough associated with chronic obstructive pulmonary disease (COPD), or asthma. For example, the present disclosure relates to a method for treating the symptoms of cough and urge to cough associated with a respiratory disease. For example, the present disclosure relates to a method of treatment of the symptoms of cough and/or urge to cough associated with a respiratory disease or disorder mediated by a P2X3 or P2X2/3 receptor antagonist.

The present disclosure also provides methods of treatment of a respiratory disease, wherein the respiratory symptoms are mediated by P2X3 and/or P2X2/3 receptor activation. The method can include administering to the subject an effective amount of a compound of Formula (I). The method can include administering any of the embodiments of Formula (I) set forth herein.

The present disclosure also provides compounds for use in treating respiratory symptoms mediated by P2X3 and/or P2X2/3 receptor activation (e.g., cough or chronic cough). The present disclosure also provides that compounds described herein can be used in the manufacture of a medicament for use in treating a respiratory disease mediated by P2X3 and/or P2X2/3 receptor activation and sensitization (e.g., cough or chronic cough).

In certain embodiments, the respiratory disease to be treated or prevented may be chronic cough. For example, the present disclosure relates to methods for reducing daytime cough in idiopathic/treatment-resistant chronic cough. In some embodiments, a subject with chronic cough has as many as 40 coughs per hour or more over a period of 24 hours (e.g., at least 25 coughs per hour). In some embodiments, the chronic cough is not obviously caused by an underlying disease or ailment. For instance, the chronic cough can be caused by persistent endogenous over-activation of a P2X3 or a P2X2/3 receptor. Such activation may not be the result of a separate ailment. In certain embodiments, the symptom or disorder to be treated is neuronal hypersensitivity underlying chronic cough.

Without wishing to be bound by any particular theory, in some embodiments, the present methods of the present disclosure can work by antagonizing and ultimately modulating (e.g., reducing) the activity of P2X3 and/or P2X2/3 receptors. This in turn can have the effect of modulating (e.g., down regulating) the function of nodose and jugular afferent fibers in mammalian airways. This process can have the global effect of reducing the neuronal signals that trigger the urge to cough, e.g., in a patient suffering from acute, sub-acute or chronic cough. Without wishing to be bound by any theory, Compound 16 may be an efficacious treatment for chronic coughing. Further without wishing to be bound by theory, the P2X3 receptor modulators described herein can adjust and/or attenuate the neuronal hypersensitivity underlying chronic cough.

In many embodiments of the present disclosure, the disorder to be treated or prevented is urge to cough associated with a respiratory disease.

For example, the methods disclosed herein relate to treating, preventing or ameliorating the respiratory diseases and disorders described herein, or symptoms thereof, described herein in a patient in need thereof by administering a compound selected from Compounds 1-39. For example, the compound is selected from Compounds 6, 7, 13, 17, 21, 28, 35 and 38. For example, the compound is Compound 16.

In some instances, preferred embodiments from one group can be combined with preferred embodiments from another group. For instance, in one preferred embodiment $R_1$ is —$CH_3$. In another preferred embodiment, $R_2$ is —$SO_2NH_2$. According to the present disclosure, the two preferred embodiments disclosed above can be combined to give a preferred compound wherein $R_1$ is —$CH_3$ and $R_2$ is —$SO_2NH_2$.

In certain embodiments of Formula (I), $R^1$ is methyl.

In certain embodiments of Formula (I), $R^1$ is hydrogen.

In certain embodiments of Formula (I), $R^2$ is haloalkyl, aminosulfonyl, alkylsulfonyl alkylcarbonyl or carboxyalkyl.

In certain embodiments of Formula (I), $R^2$ is haloalkyl, where alkyl is methyl.

In certain embodiments of Formula (I), $R^2$ is aminosulfonyl.

In certain embodiments of Formula (I), $R^2$ is carboxyalkyl.

In certain embodiments of Formula (I), $R^2$ is alkylcarbonyl.

In certain embodiments of Formula (I), where $R^1$ or $R^2$ is alkyl or contains an alkyl moiety, such alkyl is preferably lower alkyl, i.e. $C_1$-$C_6$ alkyl, and more preferably $C_1$-$C_4$ alkyl.

Representative compounds in accordance with the methods of described herein are shown in Table 1.

TABLE 1

| Compound # | Structure | Name |
|---|---|---|
| 1 | 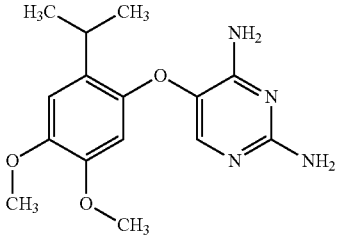 [SMILES: COc1cc(Oc2cnc(N)nc2N)c(C(C)C)cc1OC] | 5-(2-Isopropyl-4,5-dimethoxy-phenoxy)-pyrimidine-2,4-diamine |
| 2 | 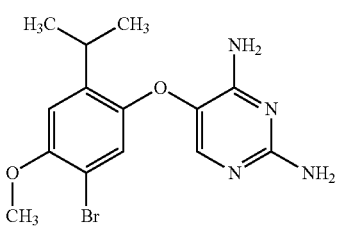 | 5-(5-Bromo-2-isopropyl-4-methoxy-phenoxy)-pyrimidine-2,4-diamine |

TABLE 1-continued

| Compound # | Structure | Name |
|---|---|---|
| 3 | 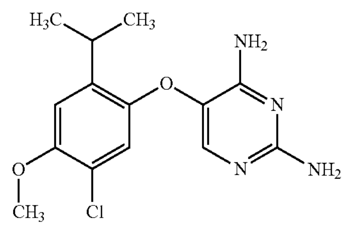 [SMILES: COc1cc(C(C)C)c(Oc2cnc(N)nc2N)cc1Cl] | 5-(5-Chloro-2-isopropyl-4-methoxy-phenoxy)-pyrimidine-2,4-diamine |
| 4 | 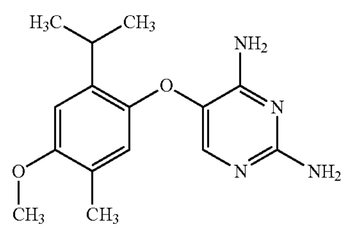 [SMILES: COc1cc(C(C)C)c(Oc2cnc(N)nc2N)cc1C] | 5-(2-Isopropyl-4-methoxy-5-methyl-phenoxy)-pyrimidine-2,4-diamine |
| 5 | 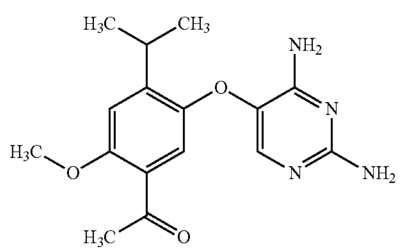 [SMILES: COc1cc(C(C)C)c(Oc2cnc(N)nc2N)cc1C(C)=O] | 1-[5-(2,4-Diamino-pyrimidin-5-yloxy)-4-isopropyl-2-methoxy-phenyl]-ethanone |
| 6 | 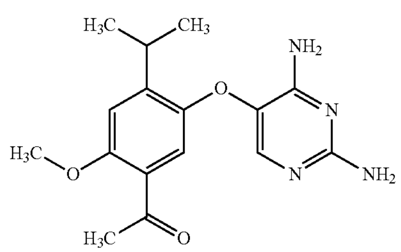 [SMILES: COc1cc(C(C)C)c(Oc2cnc(N)nc2N)cc1C(C)=O] | 5-(2,4-Diamino-pyrimidin-5-yloxy)-4-isopropyl-2-methoxy-benzamide |
| 7 | 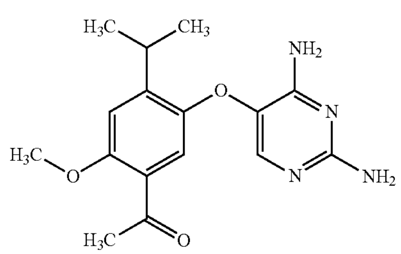 [SMILES: COc1cc(C(C)C)c(Oc2cnc(N)nc2N)cc1C(C)=O] | 5-(2,4-Diamino-pyrimidin-5-yloxy)-4-isopropyl-2-methoxy-benzoic acid |
| 8 | 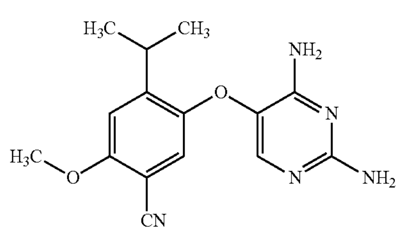 [SMILES: COc1cc(C(C)C)c(Oc2cnc(N)nc2N)cc1C#N] | 5-(2,4-Diamino-pyrimidin-5-yloxy)-4-isopropyl-2-methoxy-benzonitrile |

TABLE 1-continued

| Compound # | Structure | Name |
|---|---|---|
| 9 | 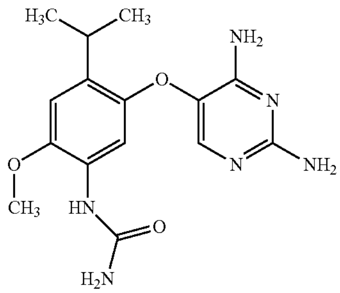 [SMILES: COc1cc(C(C)C)c(Oc2cnc(N)nc2N)cc1NC(N)=O] | [5-(2,4-Diamino-pyrimidin-5-yloxy)-4-isopropyl-2-methoxy-phenyl]-urea |
| 10 | 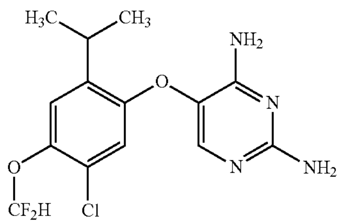 [SMILES: CC(C)c1cc(OC(F)F)c(Cl)cc1Oc1cnc(N)nc1N] | 5-(5-Chloro-4-difluoromethoxy-2-isopropyl-phenoxy)-pyrimidine-2,4-diamine |
| 11 | 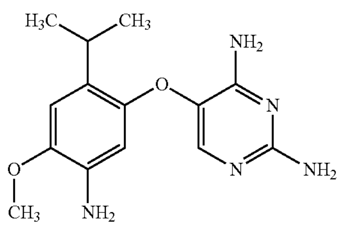 [SMILES: COc1cc(C(C)C)c(Oc2cnc(N)nc2N)cc1N] | 5-(5-Amino-2-isopropyl-4-methoxy-phenoxy)-pyrimidine-2,4-diamine |
| 12 | 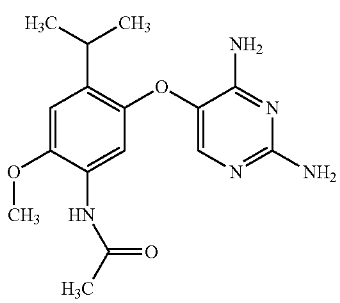 [SMILES: COc1cc(C(C)C)c(Oc2cnc(N)nc2N)cc1NC(C)=O] | N-[5-(2,4-Diamino-pyrimidin-5-yloxy)-4-isopropyl-2-methoxy-phenyl]-acetamide |
| 13 | 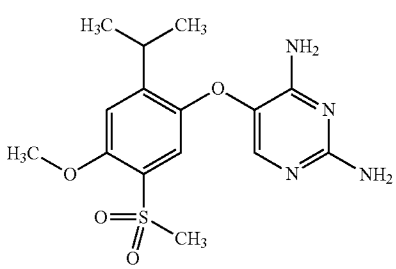 [SMILES: COc1cc(C(C)C)c(Oc2cnc(N)nc2N)cc1S(C)(=O)=O] | 5-(2-Isopropyl-5-methanesulfonyl-4-methoxy-phenoxy)-pyrimidine-2,4-diamine |
| 14 | 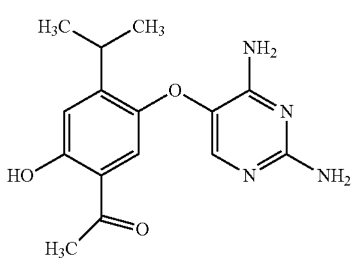 [SMILES: CC(=O)c1cc(Oc2cnc(N)nc2N)c(C(C)C)cc1O] | 1-[5-(2,4-Diamino-pyrimidin-5-yloxy)-2-hydroxy-4-isopropyl-phenyl]-ethanone |

TABLE 1-continued

| Compound # | Structure | Name |
|---|---|---|
| 15 | 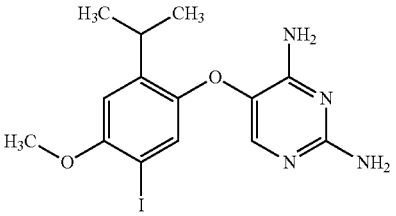 [SMILES: COc1cc(C(C)C)c(Oc2cnc(N)nc2N)cc1I] | 5-(5-Iodo-2-isopropyl-4-methoxy-phenoxy)-pyrimidine-2,4-diamine |
| 16 | 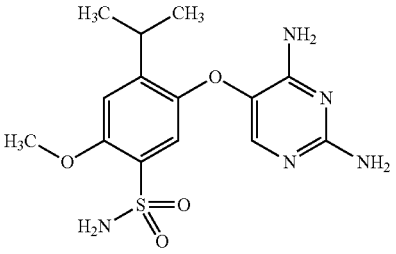 [SMILES: COc1cc(C(C)C)c(Oc2cnc(N)nc2N)cc1S(N)(=O)=O] | 5-(2,4-Diamino-pyrimidin-5-yloxy)-4-isopropyl-2-methoxy-benzenesulfonamide |
| 17 | 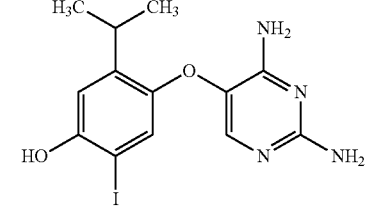 [SMILES: CC(C)c1cc(O)c(I)cc1Oc1cnc(N)nc1N] | 4-(2,4-Diamino-pyrimidin-5-yloxy)-2-iodo-5-isopropyl-phenol |
| 18 | 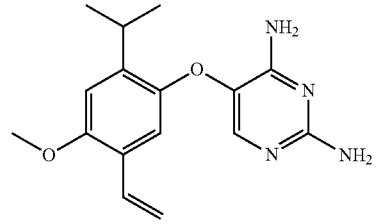 [SMILES: C=Cc1cc(Oc2cnc(N)nc2N)c(C(C)C)cc1OC] | 5-(2-Isopropyl-4methoxy-5-vinyl-phenoxy)-pyrimidine-2,4-diamine |
| 19 | 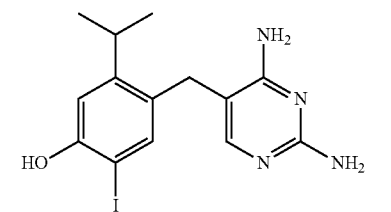 [SMILES: CC(C)c1cc(O)c(I)cc1Cc1cnc(N)nc1N] | 4-(2,4-Diamino-pyrimidin-5-ylmethyl)-2-iodo-5-isopropyl-phenol |
| 20 | 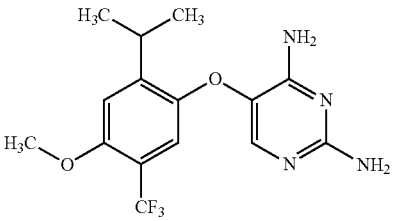 [SMILES: COc1cc(C(C)C)c(Oc2cnc(N)nc2N)cc1C(F)(F)F] | 5-(2-Isopropyl-4-methoxy-5-trifluoromethyl-phenoxy)-pyrimidine-2,4-diamine |

TABLE 1-continued

| Compound # | Structure | Name |
|---|---|---|
| 21 | 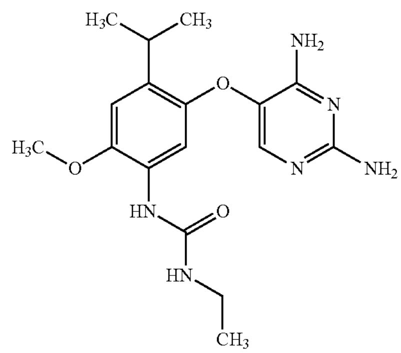 [SMILES: CCNC(=O)Nc1cc(Oc2cnc(N)nc2N)c(C(C)C)cc1OC] | 1-[5-(2,4-Diamino-pyrimidin-5-yloxy)-4-isopropyl-2-methoxy-phenyl]-3-ethyl-urea |
| 22 | 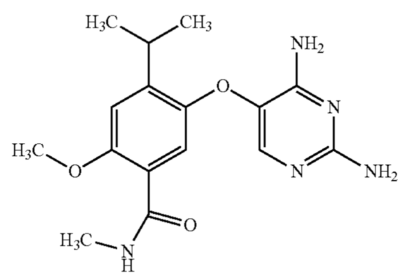 [SMILES: CNC(=O)c1cc(Oc2cnc(N)nc2N)c(C(C)C)cc1OC] | 5-(2,4-Diamino-pyrimidin-5-yloxy)-4-isopropyl-2-methoxy-N-methyl-benzamide |
| 23 | 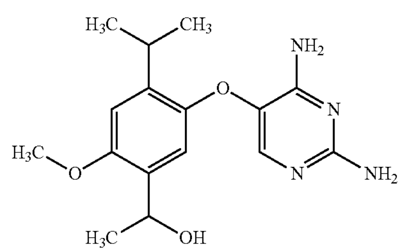 [SMILES: COc1cc(C(C)C)c(Oc2cnc(N)nc2N)cc1C(C)O] | 1-[5-(2,4-Diamino-pyrimidin-5-yloxy)-4-isopropyl-2-methoxy-phenyl]-ethanol |
| 24 | 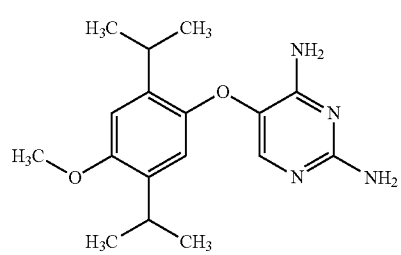 | 5-(2,5-Diisopropyl-4-methoxy-phenoxy)-pyrimidine-2,4-diamine |
| 25 | 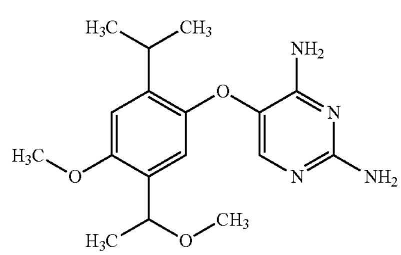 [SMILES: COc1cc(C(C)C)c(Oc2cnc(N)nc2N)cc1C(C)OC] | 5-[2-Isopropyl-4-methoxy-5-(1-methoxy-ethyl)-phenoxy]-pyrimidine-2,4-diamine |

TABLE 1-continued

| Compound # | Structure | Name |
|---|---|---|
| 26 | 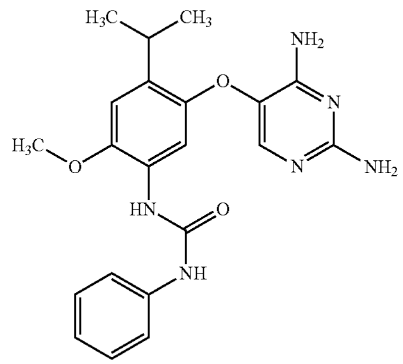 [SMILES: COc1cc(C(C)C)c(Oc2cnc(N)nc2N)cc1NC(=O)Nc1ccccc1] | 1-[5-(2,4-Diamino-pyrimidin-5-yloxy)-4-isopropyl-2-methoxy-phenyl]-3-phenyl-urea |
| 27 | 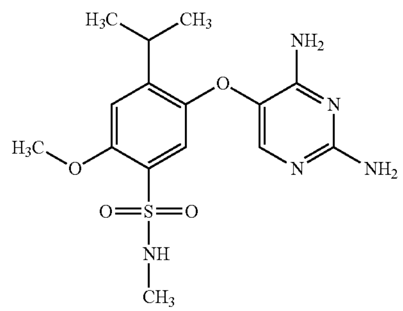 [SMILES: CNS(=O)(=O)c1cc(Oc2cnc(N)nc2N)c(C(C)C)cc1OC] | 5-(2,4-Diamino-pyrimidin-5-yloxy)-4-isopropyl-2-methoxy-N-methyl-benzenesulfonamide |
| 28 | 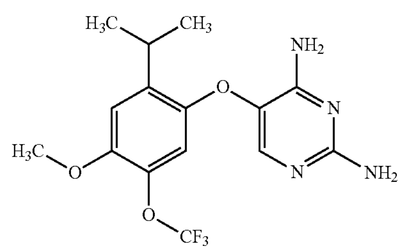 [SMILES: COc1cc(C(C)C)c(Oc2cnc(N)nc2N)cc1OC(F)(F)F] | 5-(2-Isopropyl-4-methoxy-5-trifluoromethoxy-phenoxy)-pyrimidine-2,4-diamine |
| 29 | 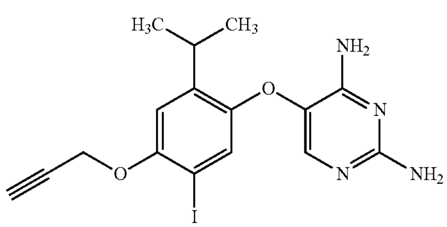 [SMILES: C#CCOc1cc(C(C)C)c(Oc2cnc(N)nc2N)cc1I] | 5-(5-Iodo-2-isopropyl-4-prop-2-ynyloxy-phenoxy)-pyrimidine-2,4-diamine |
| 30 | 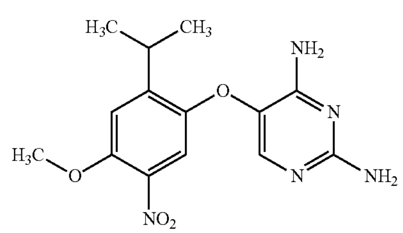 [SMILES: COc1cc(C(C)C)c(Oc2cnc(N)nc2N)cc1[N+](=O)[O-]] | 5-(2-Isopropyl-4-methoxy-5-nitro-phenoxy)-pyrimidine-2,4-diamine |
| 31 | 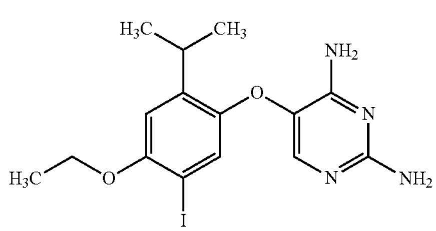 [SMILES: CCOc1cc(C(C)C)c(Oc2cnc(N)nc2N)cc1I] | 5-(4-Ethoxy-5-iodo-2-isopropyl-phenoxy)-pyrimidine-2,4-diamine |

TABLE 1-continued

| Compound # | Structure | Name |
|---|---|---|
| 32 | 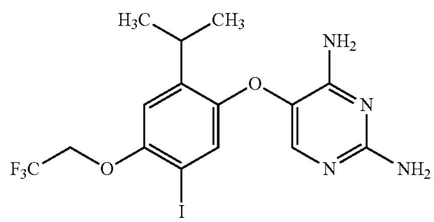 [SMILES: CC(C)c1cc(OCC(F)(F)F)c(I)cc1Oc1cnc(N)nc1N] | 5-[5-Iodo-2-isopropyl-4-(2,2,2-trifluoro-ethoxy)-phenoxyl]-pyrimidine-2,4-diamine |
| 33 | 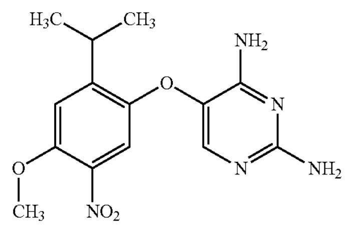 [SMILES: COc1cc(C(C)C)c(Oc2cnc(N)nc2N)cc1[N+](=O)[O-]] | 5-(2-Isopropyl-4-methoxy-5-nitro-phenoxy)-pyrimidine-2,4-diamine |
| 34 | 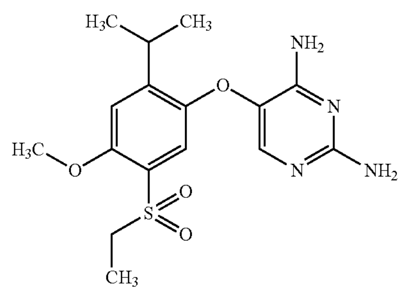 [SMILES: CCS(=O)(=O)c1cc(Oc2cnc(N)nc2N)c(C(C)C)cc1OC] | 5-(5-Ethanesulfonyl-2-isopropyl-4-methoxy-phenoxy)-pyrimidine-2,4-diamine |
| 35 | 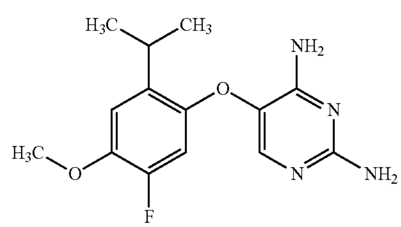 [SMILES: COc1cc(C(C)C)c(Oc2cnc(N)nc2N)cc1F] | 5-(5-Fluoro-2-isopropyl-4-methoxy-phenoxy)-pyrimidine-2,4-diamine |
| 36 | 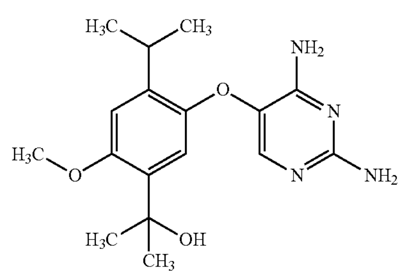 [SMILES: COc1cc(C(C)C)c(Oc2cnc(N)nc2N)cc1C(C)(C)O] | 2-[5-(2,4-Diamino-pyrimidin-5-yloxy)-4-isopropyl-2-methoxy-phenyl]-propan-2-ol |
| 37 | 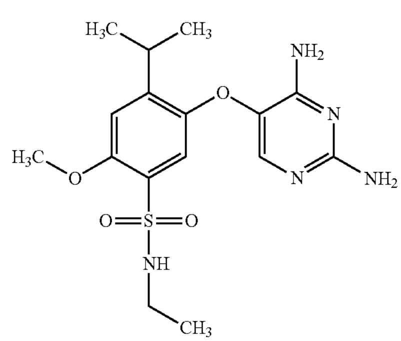 [SMILES: CCNS(=O)(=O)c1cc(Oc2cnc(N)nc2N)c(C(C)C)cc1OC] | 5-(2,4-Diamino-pyrimidin-5-yloxy)-N-ethyl-4-isopropyl-2-methoxy-benzenesulfonamide |

TABLE 1-continued

| Compound # | Structure | Name |
|---|---|---|
| 38 | 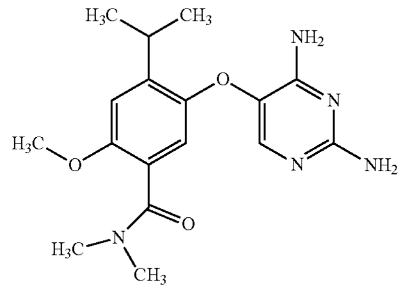 [SMILES: COc1cc(C(C)C)c(Oc2cnc(N)nc2N)cc1C(=O)N(C)C] | 5-(2,4-Diamino-pyrimidin-5-yloxy)-4-isopropyl-2-methoxy-N,N-dimethyl-benzamide |

Synthesis

Compounds of the present disclosure can be made by a variety of methods depicted in the illustrative synthetic reaction schemes shown and described below. Syntheses of compounds for use in the methods described herein can also be performed according to teachings presented in, for example, U.S. Pat. Nos. 7,858,632; 8,008,313; 8,003,788; 7,531,547; 7,741,484 and 7,799,796, each of which is specifically incorporated herein in its entirety.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present disclosure can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates another synthetic procedure usable to prepare specific compounds of Formula (I) above, wherein $R^3$, $R^4$, $R^d$, and $R^e$ are as defined herein.

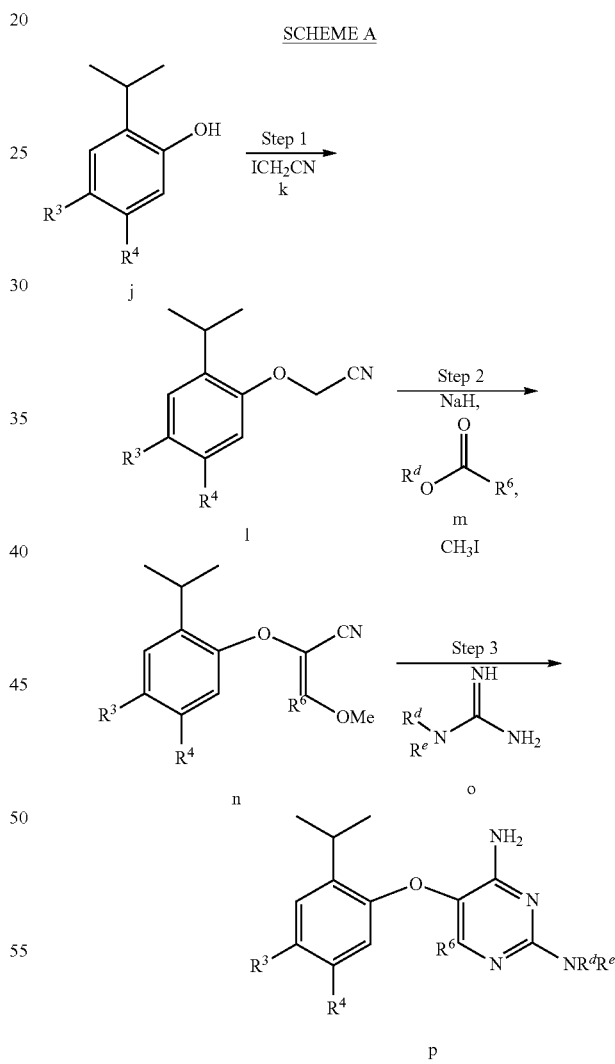

In step 1 of Scheme A, an O-alkylation is carried out by reaction of phenol j with a haloacetonitrile such as iodoacetonitrile k, to afford cyano ether l. Numerous substituted phenols j are either commercially available or may be prepared by techniques well known in the art for use in step 1. For example, substituted aldehydes may be converted to the corresponding phenols j via Baeyer-Villiger oxidation using peracid such as mCPBA, as illustrated in the experimental examples below. The alkylation of step 1 may be effected in the presence of mild base under polar aprotic solvent conditions.

In step 2, a cyano enol ether compound n is formed by treatment of cyano ether l with a strong base such as sodium hydride, followed by introduction of ester m to form an enolate (not shown), that in turn is alkylated by addition of iodomethane or other alkyl halide. This step may be carried out under polar aprotic solvent conditions.

In step 3 cyano enol ether n is reacted with guanidine compound o in the presence of base, under polar aprotic conditions, to yield diaminopyrimidine (p). The diaminopyrimidine (p) is a compound of Formula (I) usable in the methods described herein.

Numerous variations on the procedure of Scheme A are possible and will be readily apparent to those skilled in the art.

Specific details for producing compounds of the present disclosure are described in the Examples section below.

Use

The present disclosure provides methods for treating a respiratory disease mediated by a $P2X_3$ or $P2X_{2/3}$ receptor antagonist, said method comprising administering to a subject in need thereof an effective amount of a compound of Formula (I):

Exemplary respiratory diseases treatable with the methods described herein include sub-acute or chronic cough, treatment-resistant cough, idiopathic chronic cough, post-viral cough, iatrogenic cough (e.g., as induced by ACE-inhibitors), idiopathic pulmonary fibrosis or cough associated with smoking or a form of bronchitis. A disease treatable by the methods and compounds described herein includes urge to cough associated with any respiratory disease, for example urge to cough associated with chronic obstructive pulmonary disease (COPD), asthma or bronchospasm.

In certain embodiments, the respiratory disease may be chronic cough.

In many embodiments, the disease is urge to cough associated with a respiratory disease.

In one or more embodiments, the compounds described herein can result in a reduction of objective daytime cough counts in a subject with chronic cough (e.g., refractory chronic cough). For instance, administration of the compounds described herein, or a pharmaceutically acceptable salt thereof to a subject in need thereof can result in a reduction in objective daytime cough counts of between 1% and 99%. For instance, the objective daytime cough count can be reduced by between 50% and 90%, or cough count can be reduced by 75%. In addition, there may also be a significant reduction in daytime, and total 2 h cough count frequency, as well as cough severity score.

Administration and Pharmaceutical Composition

For example, the present disclosure relates to a method for treating the symptoms of cough and urge to cough associated with a respiratory disease by administering a compound of Formula (I). For example, the present disclosure relates to a method of treatment of the symptoms of cough and/or urge to cough associated with a respiratory disease or disorder mediated by a P2X3 or P2X2/3 receptor antagonist by administering a compound of Formula (I).

For example, the present disclosure relates to methods for reducing daytime cough in idiopathic/treatment-resistant chronic cough. The present disclosure also relates to a method of treating neuronal hypersensitivity underlying chronic cough.

For example, the methods described herein relate to treating, preventing or ameliorating the respiratory diseases and disorders described herein, or symptoms thereof, described herein in a patient in need thereof by administering a compound selected from Compounds 1-39. For example, the compound is selected from Compounds 6, 7, 13, 17, 21, 28, 35 and 38. For example, the compound is Compound 16.

The present disclosure includes pharmaceutical compositions comprising at least one compound as described herein, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds described herein will be administered in a therapeutically effective amount by any of the acceptable modes of administration for agents that serve similar utilities. Suitable dosage ranges are typically 1-500 mg daily or twice daily; in some embodiments, daily dosage ranges are 1-400 mg daily or twice daily; in some embodiments, daily dosage ranges are 1-300 mg daily or twice daily; in some embodiments, daily dosage ranges are 1-200 mg daily or twice daily; in some embodiments, daily dosage ranges are 1-100 mg daily or twice daily; in some embodiments, daily dosage ranges are 1-50 mg daily or twice daily; in some embodiments, daily dosage ranges are 2.5-500 mg daily or twice daily; in some embodiments, daily dosage ranges are 2.5-400 mg daily or twice daily; in some embodiments, daily dosage ranges are 2.5-300 mg daily or twice daily; in some embodiments, daily dosage ranges are 2.5-200 mg daily or twice daily; in some embodiments, daily dosage ranges are 2.5-100 mg daily or twice daily; in some embodiments, daily dosage ranges are 2.5-50 mg daily or twice daily; in some embodiments, daily dosage ranges are 5-500 mg daily or twice daily; in some embodiments, daily dosage ranges are 5-400 mg daily or twice daily; in some embodiments, daily dosage ranges are 5-300 mg daily or twice daily; in some embodiments, daily dosage ranges are 5-200 mg daily or twice daily; in some embodiments, daily dosage ranges are 5-100 mg daily or twice daily; in some embodiments, daily dosage ranges are 5-50 mg daily or twice daily; in some embodiments, daily dosage ranges are 10-500 mg daily or twice daily; in some embodiments, daily dosage ranges are 10-400 mg daily or twice daily; in some embodiments, daily dosage ranges are 10-300 mg daily or twice daily; in some embodiments, daily dosage ranges are 10-200 mg daily or twice daily; daily dosage ranges are 10-100 mg daily or twice daily; in some embodiments, daily dosage ranges are 10-50 mg daily or twice daily, depending upon numerous factors such as the severity of the disease to be treated, the age and relative health of the subject, the potency of the compound used, the route and form of administration, the indication towards which the administration is directed, and the preferences and experience of the medical practitioner involved. Suitable dosage ranges can also include dosages comprising 1-500 mg multiple times (e.g., 3-4 times) per day.

For instance, in some embodiments, the compounds described herein can be administered at a dosage of about 500 mg once, twice or multiple times daily. In some embodiments, the compounds described herein can be administered at a dosage of about 1 mg, 2.5 mg, 5 mg, 7.5 mg, 10 mg, 15 mg, 20 mg, 25 mg, 30 mg, 40 mg, 50 mg, 100 mg, 150 mg, 200 mg, 300 mg, 400 mg, or 500 mg once, twice or multiple times daily.

The duration of treatment can last for days, weeks, months or years. In some embodiments, treatment (e.g., administration of a compound described herein or a pharmaceutically acceptable salt thereof) lasts for two weeks. In some embodiments, treatment lasts one month. In some embodiments, treatment can proceed indefinitely. In some embodiments of the present disclosure, a subject can be treated with a compound of Formula (I) at a dosage of no greater than 500 mg once or twice daily for days, weeks, months or years, including indefinitely. In some embodiments of the present disclosure, a subject can be treated with a compound of Formula (I) at a dosage of no greater than about 1 mg, 2.5 mg, 5 mg, 7.5 mg, 10 mg, 15 mg, 20 mg, 25 mg, 30 mg, 40 mg, 50 mg, 100 mg, 150 mg, 200 mg, 300 mg, 400 mg, or 500 mg once or twice daily.

As used herein, treatment for a matter of days includes treatment for 1 day, 2 days, 3 days, 4 days, 5 days, 6 days, 7 days, 8 days, 9 days or 10 days, or longer.

As used herein, treatment for a matter of weeks includes treatment for at least one week, or for two weeks, or for three weeks, or for four weeks, or for five weeks, or for six weeks, or for seven weeks, or for eight weeks, or longer.

As used herein, treatment for a matter of months includes treatment for at least one month, or for two months, or for three months, or for four months, or for five months, or for six months, or longer.

As used herein, treatment for a matter of years includes treatment for at least one year, or for two years, or for three years, or for four years, or for five years, or longer.

As used herein, treatment indefinitely refers to on-going treatment as may be appropriate when treating a chronic condition.

One of ordinary skill in the art of treating such diseases will be able, without undue experimentation and in reliance upon personal knowledge and the disclosure of this application, to ascertain a therapeutically effective amount of the compounds described herein for a given disease.

Compounds described herein may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds described herein, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds described herein may be formulated in a wide variety of oral administration dosage forms. The pharmaceutical compositions and dosage forms may comprise a compound or compounds of the present disclosure or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds described herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds described herein may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, oral tape or lozenge itself, or it can be the appropriate number of any of these in packaged form.

Other suitable pharmaceutical carriers and their formulations are described in *Remington: The Science and Practice of Pharmacy* (1995), edited by E. W. Martin, Mack Publishing Company, 19th edition, Easton, Pa. Representative pharmaceutical formulations containing a compound as described herein are described below.

EXAMPLES

The following preparations and examples are given to enable those skilled in the art to more clearly understand and to practice the present disclosure. They should not be considered as limiting the scope of the present disclosure, but merely as being illustrative and representative thereof.

Example 1. 5-(5-Bromo-2-isopropyl-4-methoxy-phenoxy)-pyrimidine-2,4-diamine

The synthetic procedure used in this Example is outlined in Scheme B.

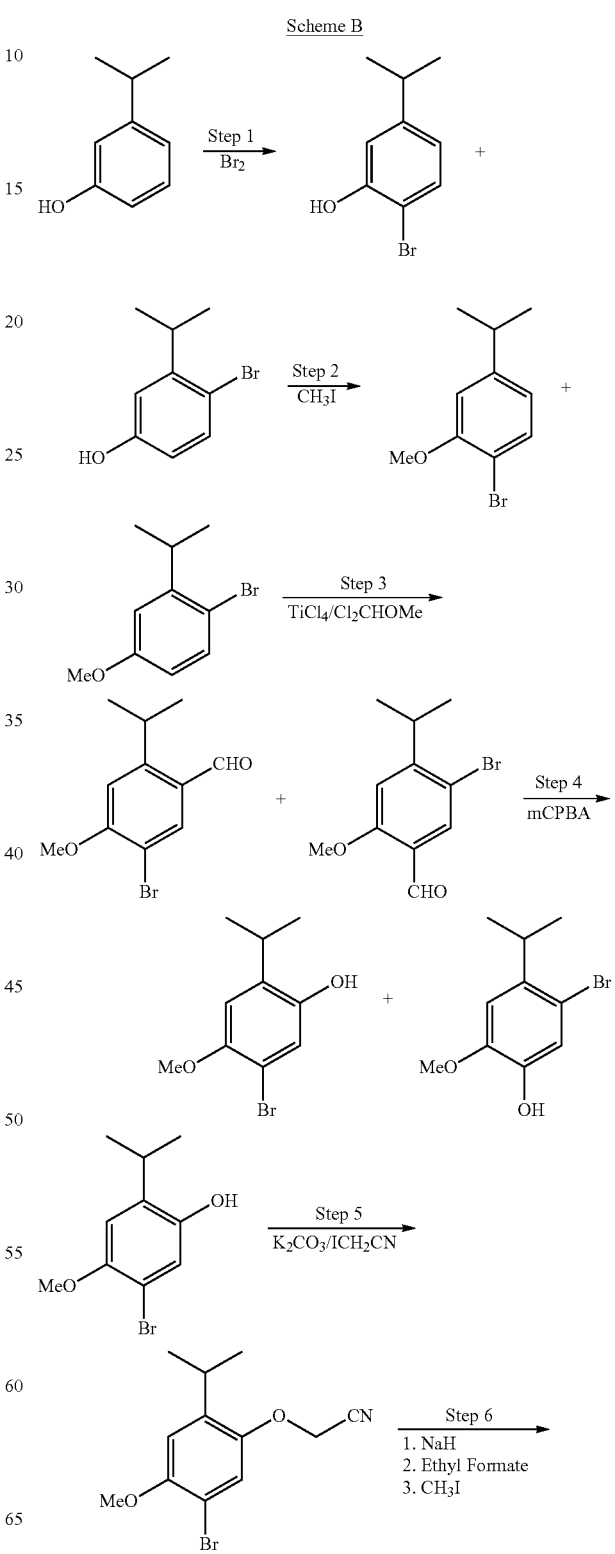

-continued

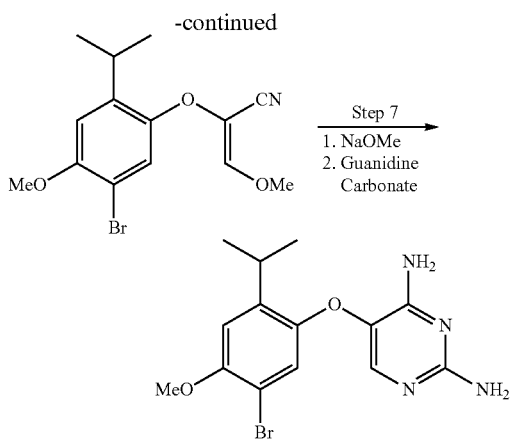

Step 1. 2-Bromo-5-isopropyl-phenol

A solution of 3-isopropyl phenol (4.975 g, 36.5 mmol) in 37 mL of CCl$_4$ was cooled to −20° C. Bromine (1.9 mL, 38.4 mmol) was dissolved in 5.0 mL CCl$_4$ and added drop-wise at such a rate that the internal temperature was maintained below −10° C. The mixture was allowed to warm to room temperature. After 12 hours the mixture was taken up in 100 mL CH$_2$Cl$_2$, washed with H$_2$O and then with brine. The combined organics were dried over Na$_2$SO$_4$, filtered and concentrated in vacuo to give 8.663 g of a 1:1 mixture of 2-bromo-5-isopropyl-phenol and 4-bromo-5-isopropyl phenol as an oil). These two isomers were inseparable and were used together in step 2 below.

Step 2. 1-Bromo-4-isopropyl-2-methoxy-benzene

To a mixture of 2-bromo-5-isopropyl-phenol and 4-bromo-5-isopropyl phenol from step 1 (8.663 g, 40.3 mmol), K$_2$CO$_3$ (16.710 g, 120.9 mmol) in 50 mL DMF, was added iodomethane (3.0 mL, 48.3 mmol) with mechanical stirring. The mixture was warmed to 50° C. for 4 hours. After cooling to room temperature 300 mL H$_2$O was added and the solution was extracted with diethyl ether (Et$_2$O), washed with H$_2$O and washed with brine. The combined organics were dried over MgSO$_4$, filtered and concentrated in vacuo to give 1-bromo-4-isopropyl-2-methoxy-benzene and 1-bromo-2-isopropyl-4-methoxy-benzene (6.621 g, 72%) as a 1:1 inseparable mixture in the form of an oil. This mixture of regioisomers was used directly in step 3 below.

Step 3. 5-Bromo-2-isopropyl-4-methoxy-benzaldehyde

To a solution of 1-bromo-4-isopropyl-2-methoxy-benzene and 1-bromo-2-isopropyl-4-methoxy-benzene from step 2 (6.621 g, 28.9 mmol) in 100 mL 1,2 dichloroethane was added TiCl$_4$ (6.3 mL, 57.8 mmol) at 0° C. After 10 minutes, dichloromethoxymethane (Cl$_2$CHOMe) (2.6 mL, 28.9 mmol) was added and the mixture was warmed to reflux. After 3 hours the mixture was cooled poured over ice and acidified with 50 mL 2 M HCl. The resulting slurry was extracted with CH$_2$Cl$_2$, and washed with brine. The combined organics were dried over MgSO$_4$, filtered and concentrated in vacuo to give an oil. Purification via flash chromatography (96:4 hexane/ethyl acetate) afforded 5-bromo-2-isopropyl-4-methoxy-benzaldehyde and 5-bromo-4-isopropyl-2-methoxy-benzaldehyde (2.876 g, 39%, 6.621 g, 72%) as a 1:1 mixture of inseparable isomers in the form of an orange oil, which was used directly in step 4.

Step 4. 5-Bromo-2-isopropyl-4-methoxy-phenol

To a solution of 5-bromo-2-isopropyl-4-methoxy-benzaldehyde and 5-bromo-4-isopropyl-2-methoxy-benzaldehyde from step 3 (2.87 g, 11.2 mmol) in 25 mL CH$_2$Cl$_2$ was added mCPBA (2.31 g, 13.4 mmol). After 16 hours the mixture was taken up in 150 ml CH$_2$Cl$_2$ and washed with sat NaHCO$_3$, and then with brine. The combined organic layers were dried over Na$_2$SO$_4$, filtered and concentrated in vacuo to give an oil that was taken up in 50 mL MeOH and 30 mL 4M NaOH. After 2 hours the mixture was evaporated, diluted with water and acidified to pH=1 with concentrated HCl. The mixture was extracted with ethyl acetate (3×100 mL) and washed with 100 mL brine. The combined organics were dried over Na$_2$SO$_4$, filtered and evaporated to give a mixture of 5-bromo-2-isopropyl-4-methoxy-phenol and 2-bromo-5-isopropyl-4-methoxy-phenol as an orange residue. These regioisomers were separable by flash chromatography (gradient: hexane, 7:3, 1:1 hexane/CH$_2$Cl$_2$) to afford 5-bromo-2-isopropyl-4-methoxy-phenol (0.929, 34%) as a yellow oil which was used in the following step, and 2-bromo-5-isopropyl-4-methoxy-phenol (0.404 g, 15%) as a yellow solid.

Step 5. (5-Bromo-2-isopropyl-4-methoxy-phenoxy)-acetonitrile

To a mixture of 5-bromo-2-isopropyl-4-methoxy-phenol from step 4 (0.831 g, 3.4 mmol) and K$_2$CO$_3$ (0.562 g, 4.1 mmol) in 17 mL dimethyl formamide (DMF) was added iodoacetonitrile (0.594 g, 3.6 mmol). The mixture was warmed to 60° C. for 30 minutes and then allowed to cool to room temperature. After cooling to room temperature the mixture was taken up in 50 mL of H$_2$O and extracted with 1:1 toluene/ethyl acetate, washed with H$_2$O and then with brine. The combined organic layers were dried over Na$_2$SO$_4$, filtered and concentrated in vacuo to give a crude solid. Purification via flash chromatography (1:1 hexane/CH$_2$Cl$_2$) afforded (5-bromo-2-isopropyl-4-methoxy-phenoxy)-acetonitrile (0.611 g, 63%) as a while solid.

Step 6. 2-(5-Bromo-2-isopropyl-4-methoxy-phenoxy)-3-methoxy-acrylonitrile

Sodium hydride (0.122 g, 5.0 mmol, 60% w/w) was washed with dry hexanes and evaporated under a stream of nitrogen. 10 mL THF was added and the mixture was cooled to 0° C. (5-Bromo-2-isopropyl-4-methoxy-phenoxy)-acetonitrile (0.577 g, 2.03 mmol) was added in portions. After 30 min ethyl formate (4.9 mL, 60.9 mmol) was added and the solution was warmed to 80° C. After 4.5 hours the mixture was cooled and 5.0 mL iodomethane was added in one portion. After 16 hours the solution was quenched with H$_2$O, concentrated in vacuo, extracted with ethyl acetate, washed with H$_2$O and then washed with brine. The combined organic layers were dried over Na$_2$SO$_4$, filtered and concentrated in vacuo. Purification via flash chromatography (9:1 hexane/ethyl acetate) afforded 2-(5-bromo-2-isopropyl-4-methoxy-phenoxy)-3-methoxy-acrylonitrile (0.319 g, 48%) as a white solid.

Step 7. 5-(5-Bromo-2-isopropyl-4-methoxy-phenoxy)-pyrimidine-2,4-diamine

To a solution of 2-(5-bromo-2-isopropyl-4-methoxy-phenoxy)-3-methoxy-acrylonitrile (0.282 g, 0.9 mmol) and guanidine carbonate (0.078 g, 0.4 mmol) in 10.0 mL dimethyl sulfoxide (DMSO) was added sodium methoxide (1.0 mL, 1.0M in MeOH). The mixture was warmed to 120° C. The methanol was collected via a short-path condenser. After 3 h the mixture was cooled and concentrated in vacuo to give a crude oil. Purification via flash chromatography (95:5 CH$_2$Cl$_2$/MeOH) afforded 17 (0.246 g, 77%) as a pink solid; Mass Spec M+H=352. The above procedure may be used with various different phenols in step 1 and/or substituted guanidines in step 7 under essentially the same reaction conditions to produce additional compounds. Additional compounds made according to the procedure of Example 1 are shown in Table 1.

Example 2. 5-(2-Isopropyl-5-methanesulfonyl-4-methoxy-phenoxy)-pyrimidine-2,4-diamine

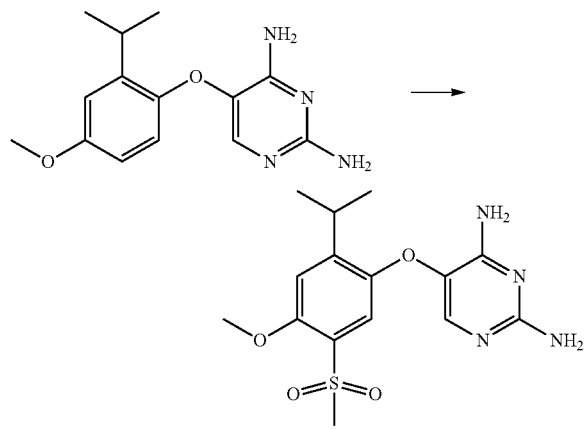

To a mixture of 5-(2-isopropyl-4-methoxy-phenoxy)-pyrimidine-2,4-diamine (0.32 g, 1.17 mmol), prepared according to Example 2, and methanesulfonic anhydride (0.81 g, 4.67 mmol) was added trifluoromethanesulfonic acid (0.45 g, 3.00 mmol), and the mixture was heated at 80° C. for 16 hrs. The reaction mixture was poured into ice water, basified with saturated NaHCO$_3$ solution and extracted into dichloromethane, which was dried over Na$_2$SO$_4$, filtered and concentrated in vacuo. The residue was purified via flash chromatography on silica gel (3% CH$_3$OH in CH$_2$Cl$_2$ with 0.1% NH$_4$OH) gave 5-(2-isopropyl-5-methanesulfonyl-4-methoxy-phenoxy)-pyrimidine-2,4-diamine as a white solid (0.248 g, 90%; 0.107 g), MS (M+H): 353.

Example 3. 5-(5-Iodo-2-isopropyl-4-methoxy-phenoxy)-pyrimidine-2,4-diamine

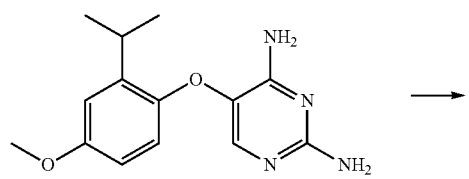

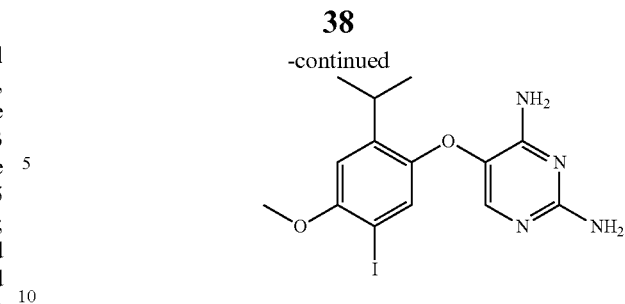

To a solution of 5-(2-isopropyl-4-methoxy-phenoxy)-pyrimidine-2,4-diamine (0.40 g, 1.44 mmol) in glacial acetic acid (4 ml) at room temperature was added a solution of iodine monochloride (0.28 g, 1.76 mmol) in glacial acetic acid (4 ml). Water (6 ml) was also added, and the reaction was stirred for 16 hours, after which another portion of iodine monochloride (0.4 g, 2.47 mmol) in glacial acetic acid (4 ml) was added. The reaction mixture was stirred for an additional hour at room temperature. The acidic mixture was basified with saturated NaHCO$_3$ solution and extracted into dichloromethane. The organic layer was dried over Na$_2$SO$_4$, filtered and concentrated in vacuo. The residue was purified via flash chromatography (5% CH$_3$OH in CH$_2$CL$_2$ with 0.1% NH$_4$OH) to give 5-(5-iodo-2-isopropyl-4-methoxy-phenoxy)-pyrimidine-2,4-diamine as beige colored solid (0.536 g, 92%). M+H 400.

Example 4. 5-(2,4-Diamino-pyrimidin-5-yloxy)-4-isopropyl-2-methoxy-benzonitrile

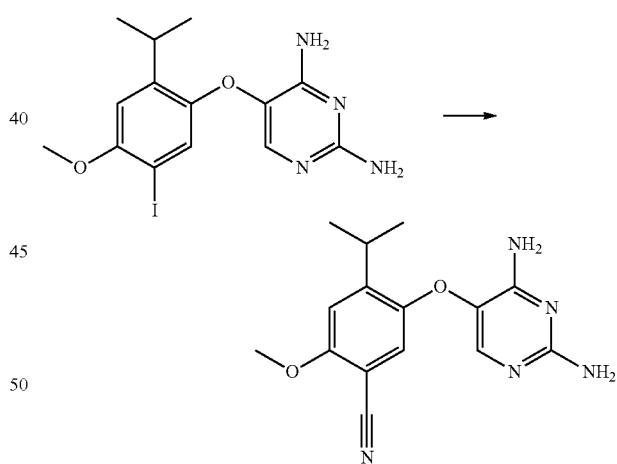

A mixture of 5-(5-iodo-2-isopropyl-4-methoxy-phenoxy)-pyrimidine-2,4-diamine (0.37 g, 0.925 mmol) and CuCN (0.12 g, 1.39 mmol) in DMF (5 ml) was heated at 120° C. for 3 hours. Water (100 ml) was added, and the precipitate was collected. The residue was triturated with methanolic dichloromethane (10% CH$_3$OH in CH$_2$Cl$_2$ with 0.1% NH$_4$OH) to release the product from its copper complex and filtered. The filtrate was concentrated and purified via flash chromatography (3% CH$_3$OH in CH$_2$Cl$_2$ with 0.1% NH$_4$OH) to give 5-(2,4-diamino-pyrimidin-5-yloxy)-4-isopropyl-2-methoxy-benzonitrile as white solid (0.12 g, 44%): M+H 300.

Example 5. 1-[5-(2,4-Diamino-pyrimidin-5-yloxy)-4-isopropyl-2-methoxy-phenyl]-ethanone and 1-[5-(2,4-Diamino-pyrimidin-5-yloxy)-2-hydroxy-4-isopropyl-phenyl]-ethanone

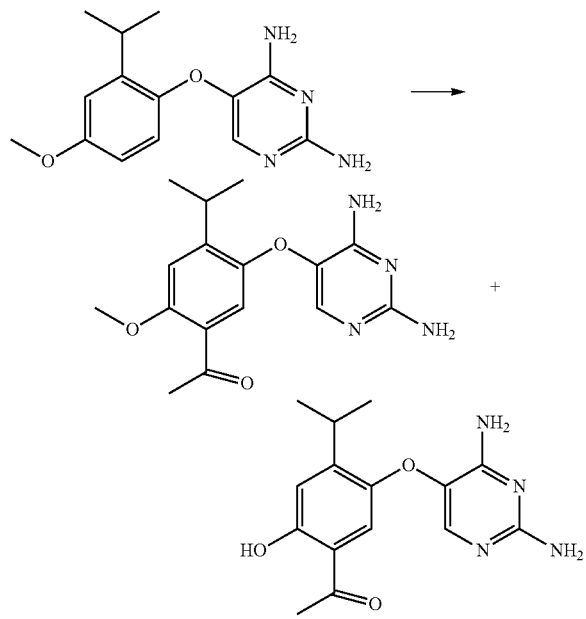

5-(2-isopropyl-4-methoxy-phenoxy)-pyrimidine-2,4-diamine in anhydrous dichloroethane (20 mL) was added to trifluoroacetic acid (0.06 mL, 0.77 mmol), acetyl chloride (0.31 mL, 4.37 mmol), and aluminum trichloride (583 mg, 4.37 mmol). After stirring for 22 hours at room temperature, water (1.2 mL) was added to the reaction at 0° C. The mixture was dried using anhydrous sodium sulfate and concentrated in vacuo. Aqueous sodium hydroxide (0.2M, 10 mL) was added to the residue and the mixture was heated at 100° C. for 1 hour. After cooling, the reaction was extracted with dichloromethane. The dichloromethane layer was dried using anhydrous magnesium sulfate, concentrated, and purified with silica gel column chromatography eluting with 96/4/0.1 dichloromethane/methanol/ammonium hydroxide to yield 1-[5-(2,4-diamino-pyrimidin-5-yloxy)-4-isopropyl-2-methoxy-phenyl]-ethanone (72 mg, 31%) as off-white solid, MS (M+H)=317. Also recovered was 1-[5-(2,4-diamino-pyrimidin-5-yloxy)-2-hydroxy-4-isopropyl-phenyl]-ethanone (43 mg, 20%) as pale yellow solid, MS (M+H)=303.

Example 6. 5-(2,4-Diamino-pyrimidin-5-yloxy)-4-isopropyl-2-methoxy-benzoic Acid

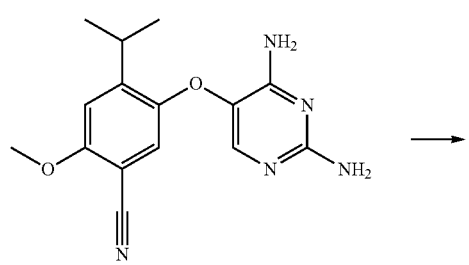

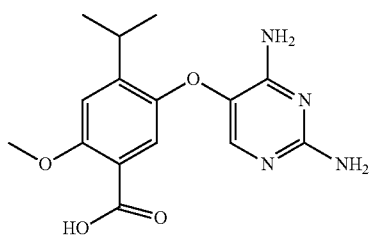

To a suspension of 5-(2,4-diamino-pyrimidin-5-yloxy)-4-isopropyl-2-methoxy-benzonitrile (50 mg, 0.17 mmol, from Example 15) in ethanol (1 mL) was added sodium hydroxide (174 mg, 4.34 mmol, dissolved in 1 mL water). After refluxing overnight, the reaction was cooled in an ice bath. Aqueous hydrochloric acid (3M) was added until the pH of the reaction was 7. The white solid precipitate was collected, washed with small amounts of water and dichloromethane, and dried to yield 5-(2,4-diamino-pyrimidin-5-yloxy)-4-isopropyl-2-methoxy-benzoic acid: (51 mg, 96%, MS (M+H)=319), which was converted to the hydrochloride salt.

Example 7. 5-(2,4-Diamino-pyrimidin-5-yloxy)-4-isopropyl-2-methoxy-benzamide

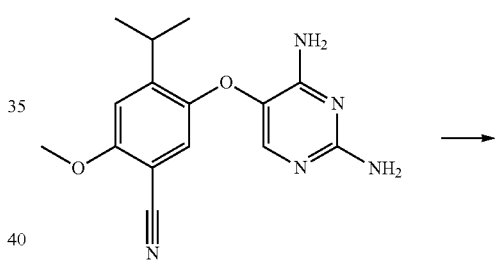

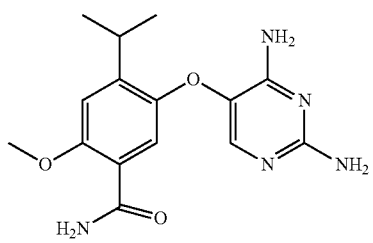

To 5-(2,4-diamino-pyrimidin-5-yloxy)-4-isopropyl-2-methoxy-benzonitrile (49 mg, 0.16 mmol, from Example 15) suspended in ethanol (1 mL) was added sodium hydroxide (64 mg, 1.60 mmol, dissolved in 1 mL water). The reaction was heated at 110° C. for 5 hours, cooled, and washed with dichloromethane (25 mL). The dichloromethane layer was concentrated and purified by preparatory TLC plates (92/8/0.5 dichloromethane/methanol/ammonium hydroxide) to yield 5-(2,4-diamino-pyrimidin-5-yloxy)-4-isopropyl-2-methoxy-benzamide as white solid (9 mg, 17%, MS (M+H)=318), which was converted to the hydrochloride salt.

Example 8. [5-(2,4-Diamino-pyrimidin-5-yloxy)-4-isopropyl-2-methoxy-phenyl]-urea

Step 1. 5-(5-Amino-2-isopropyl-4-methoxy-phenoxy)-pyrimidine-2,4-diamine

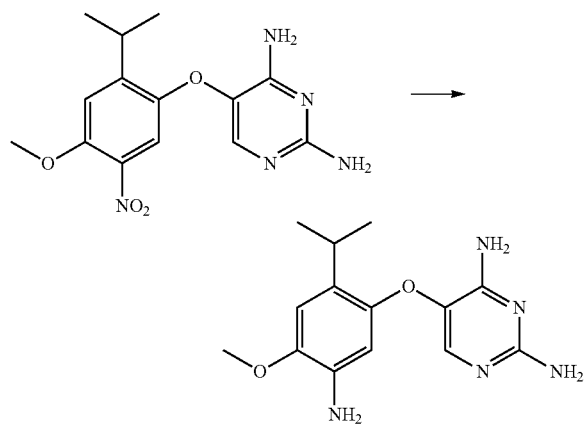

To 5-(2-isopropyl-4-methoxy-5-nitro-phenoxy)-pyrimidine-2,4-diamine (2.1 g, 6.58 mmol) suspended in ethanol (150 mL) in a Parr bomb, was added 10% palladium on charcoal (210 mg). After hydrogenation in the Parr hydrogenator overnight at 35 psi, the reaction was filtered through celite. The celite pad was washed with ethanol and ethyl acetate and the filtrate was concentrated. Purification with silica gel column chromatography (92/8/0.1 dichloromethane/methanol/ammonium hydroxide) gave 5-(5-amino-2-isopropyl-4-methoxy-phenoxy)-pyrimidine-2,4-diamine as a pale orange solid (468 mg, 25%, (M+H)$^+$=290), which was converted to the hydrochloride salt.

Step 2. [5-(2,4-Diamino-pyrimidin-5-yloxy)-4-isopropyl-2-methoxy-phenyl]-urea

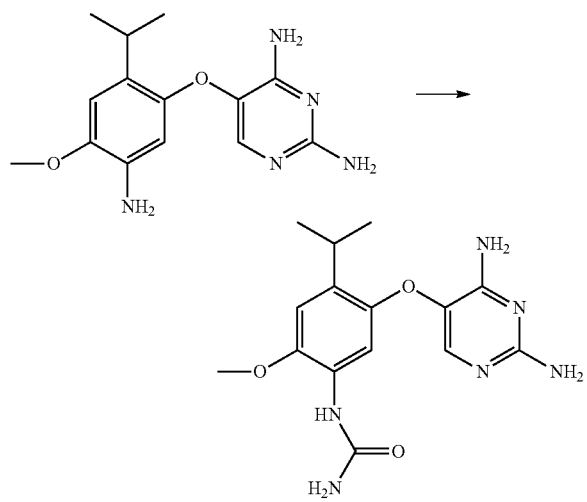

To 5-(5-amino-2-isopropyl-4-methoxy-phenoxy)-pyrimidine-2,4-diamine (314 mg, 1.09 mmol) suspended in water (3 mL) was added acetic acid (0.25 mL, 4.34 mmol). Once all solids had dissolved, sodium cyanate (71 mg, 1.09 mmol, dissolved in 1.5 mL water) was added dropwise. After 30 minutes, the reaction was concentrated and purified with silica gel column chromatography eluting with 92/8/0.1 dichloromethane/methanol/ammonium hydroxide to yield [5-(2,4-diamino-pyrimidin-5-yloxy)-4-isopropyl-2-methoxy-phenyl]-urea as an off-white solid (244 mg, 68%, M+H)$^+$=333), which was converted to a hydrochloride salt.

Example 9. N-[5-(2,4-Diamino-pyrimidin-5-yloxy)-4-isopropyl-2-methoxy-phenyl]-acetamide

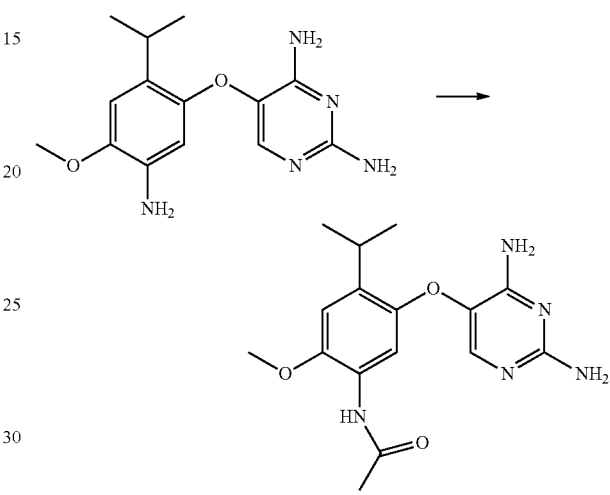

To 5-(5-amino-2-isopropyl-4-methoxy-phenoxy)-pyrimidine-2,4-diamine (100 mg, 0.35 mmol, from Example 17) dissolved in anhydrous dichloromethane (10 mL) was added anhydrous pyridine (0.03 mL, 0.38 mmol). To this reaction mixture at 0° C. was added acetyl chloride (0.03 mL, 0.38 mmol). After stirring at room temperature for 1 hour, the reaction was concentrated and purified with preparatory TLC (93/7/0.5 dichloromethane/methanol/ammonium hydroxide) to yield an off-white solid (74 mg mixture of bis- and tris-acetylated products). To this solid was added aqueous sodium hydroxide (0.2 M, 2 mL), and the mixture was refluxed for 1 hour, cooled, and washed with dichloromethane (10 mL). The dichloromethane layer was dried using anhydrous magnesium sulfate and concentrated in vacuo to yield N-[5-(2,4-diamino-pyrimidin-5-yloxy)-4-isopropyl-2-methoxy-phenyl]-acetamide as a white solid (53 mg, 46%, M+H)$^+$=332) which was converted to a hydrochloride salt:

Example 10. 5-(2-Isopropyl-4-methoxy-5-nitro-phenoxy)-pyrimidine-2,4-diamine

The synthetic procedure used in this Example is outlined in Scheme D

SCHEME D

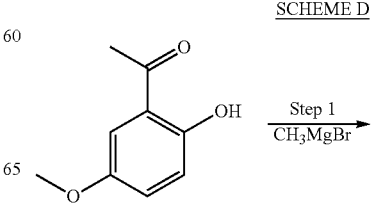

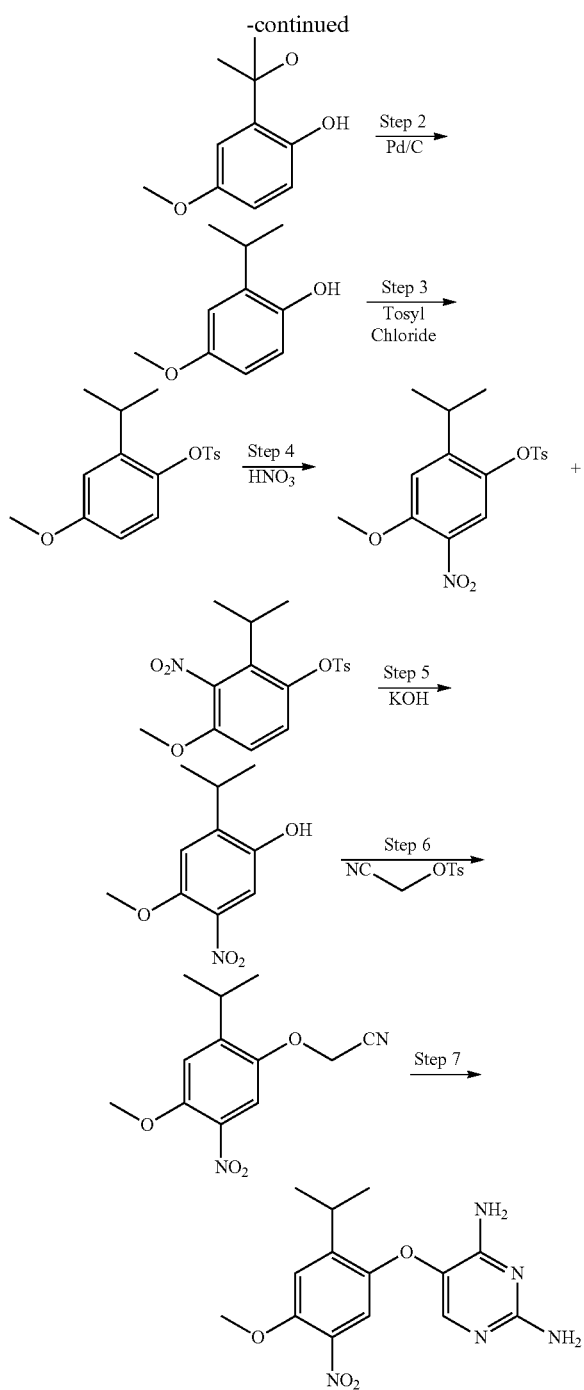

Step 1. 2-(1-Hydroxy-1-methyl-ethyl)-4-methoxy-phenol

To a solution of methyl magnesium bromide (221 ml, 665 mmol) in 800 ml THF at 0° C. was added 1-(2-hydroxy-5-methoxy-phenyl)-ethanone (20.21 g, 302 mmol) in portions over 30 min. The mixture was allowed to warm to room temperature. After 16 h the mixture was quenched by the slow addition of 10% NH$_4$Cl, carefully acidified to pH=1 (slow addition) with concentrated HCl and extracted with Et$_2$O. The combined organics were washed with H$_2$O, washed with brine, died over MgSO$_4$, filtered and concen-trated in vacuo to give 2-(1-hydroxy-1-methyl-ethyl)-4-methoxy-phenol (50.57 g, 100%) as a tan solid.

Step 2. 2-Isopropyl-4-methoxy-phenol

To a solution of 2-(1-hydroxy-1-methyl-ethyl)-4-methoxy-phenol (50.57 g, 278 mmol) in 550 ml AcOH was added 10% Pd/C (as a slurry in 20 ml H$_2$O). Ammonium formate (87.52 g, 1388 mmol) was added in portions. The mixture was warmed to 100° C. for 1 hour, cooled and filtered through a pad of celite. The celite pad was washed with ethyl acetate. The mother liquor was mixed with H$_2$O and extracted with ethyl acetate. The combined organics were washed with H$_2$O, washed with brine, dried over Na$_2$SO$_4$, filtered and concentrated in vacuo to give 2-iso-propyl-4-methoxy-phenol (44.74 g, 97%) as a pale yellow oil.

Step 3. Toluene-4-sulfonic acid 2-isopropyl-4-methoxy-phenyl Ester

To a solution of 2-isopropyl-4-methoxy-phenol (56.91 g, 342 mmol) triethylamine (57.3.0 ml, 411 mmol) in 750 ml CH$_2$Cl$_2$ was cooled to 0° C. p-Toluenesulfonyl chloride (68.54 g, 360 mmol) in 250 ml CH$_2$Cl$_2$ was added drop-wise at a rate that maintained the internal temperature<10° C. The mixture was allowed to warm to rt. After 16 h, H$_2$O was added and the mixture was extracted with CH$_2$Cl$_2$. The combined organics were washed with brine, dried with Na$_2$SO$_4$, filtered and concentrated in vacuo to afford a crude solid. Recrystallization from hexanes afforded toluene-4-sulfonic acid 2-isopropyl-4-methoxy-phenyl ester (81.67 g, 74%) as white needles.

Step 4. Toluene-4-sulfonic acid 2-isopropyl-4-methoxy-5-nitro-phenyl Ester

To a solution of toluene-4-sulfonic acid 2-isopropyl-4-methoxy-phenyl ester (19.00 g, 59 mmol) in 118 mL AcOH was added 236 ml fuming HNO$_3$ over 20 min. After 16 h the solution was pouring into a rapidly stirring slurry of 2 l of ice/H$_2$O. After 15 min the precipitate was filtered, washed with H$_2$O and dried under vacuum (50° C.) to give toluene-4-sulfonic acid 2-isopropyl-4-methoxy-5-nitro-phenyl ester (21.27 g, 98%) and toluene-4-sulfonic acid 2-isopropyl-4-methoxy-3-nitro-phenyl ester and as a pale yellow solid (7:1 inseparable mixture).

Step 5. 2-Isopropyl-4-methoxy-5-nitro-phenol

A solution of toluene-4-sulfonic acid 2-isopropyl-4-methoxy-5-nitro-phenyl ester and 2-isopropyl-4-methoxy-3-nitro-phenyl ester (21.20 g, 58 mmol) and 175 mL 2M KOH in 350 mL EtOH was warmed to 100° C. After 45 minutes the mixture was cooled, evaporated and taken up in 1 l of water. The solution was acidified to pH=1 with 12 M HCl and extracted with ethyl acetate. The combined organics were washed with H$_2$O, brine, dried over Na$_2$SO$_4$, filtered and concentrated in vacuo. The crude oil was purified via flash chromatography (gradient: 95:5 to 4:1 hexane/ethyl acetate) to afford 3-amino-2-isopropyl-5-nitro-phenol (10.03 g, 81%) as a yellow solid and 3-amino-2-isopropyl-3-nitro-phenol (1.32 g, 11%) as a yellow oil.

Step 6. (2-Isopropyl-4-methoxy-5-nitro-phenoxy)-acetonitrile

A mixture of 3-amino-2-isopropyl-5-nitrophenol (9.94 g, 47 mmol), K$_2$CO$_3$ (13.00 g, 94 mmol) and toluenesulfonic acid cyanomethyl ester (10.93 g, 52 mmol) in 500 mL DMF was warmed to 50° C. After 16 h the mixture was cooled, poured into 500 mL H₂O and extracted with toluene/ethyl acetate (1:1). The combined organics were washed with H₂O, washed with brine, filtered and concentrated in vacuo. The crude solid was recrystallized from EtOH to afford (2-isopropyl-4-methoxy-5-nitro-phenoxy)-acetonitrile (8.95 g, 76%) as a yellow crystalline solid.

Step 7. 5-(2-Isopropyl-4-methoxy-5-nitro-phenoxy)-pyrimidine-2,4-diamine

A mixture of (2-isopropyl-4-methoxy-5-nitro-phenoxy)-acetonitrile (8.785 g, 35.5 mmol) and Bredereck's reagent (14.6 mL, 70.9 mmol) was warmed to 100° C. After 45 min the mixture was evaporated under reduced pressure (50° C., 50 mtorr) to give an orange solid. The solid was added to a solution of aniline hydrochloride (9.19 g, 70.9 mmol) in 150 mL of EtOH. The mixture was warmed to reflux. After 16 hr additional aniline hydrochloride (4.596 g, 35.5 mmol) was added mixture was continued at reflux for 4 h. The solution was concentrated in vacuo and poured into H₂O. The mixture was extracted with ethyl acetate, washed with H₂O, washed with brine, dried over Na₂SO₄, and concentrated in vacuo to afford a yellow-green solid. This crude product was added to a mixture of 200 mL NMP and guanidine carbonate (17.70 g, 98 mmol) and warmed to 130° C. After 5 hours the mixture was cooled then poured onto 2 l of an ice/H₂O mixture. The resulting precipitate was filtered, washed with H₂O and dried under vacuum (50° C.). The crude solid was recrystallized from EtOH to afford 5-(2-isopropyl-4-methoxy-5-nitro-phenoxy)-pyrimidine-2,4-diamine (8.14 g, 63%, 3 steps) as a yellow crystalline solid (solvated 1:1 with EtOH). (M+H)⁺=320.

Example 11. 1-[5-(2,4-Diamino-pyrimidin-5-yloxy)-4-isopropyl-2-methoxy-phenyl]-3-ethyl-urea Step 1. 5-(5-Amino-2-Isopropyl-4-methoxy-phenoxy)-pyrimidine-2,4-diamine

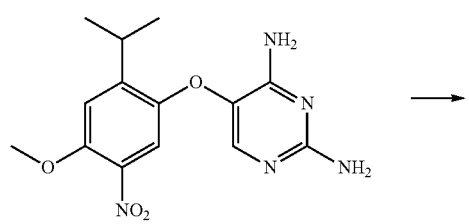

To a solution of 5-(2-isopropyl-4-methoxy-5-nitro-phenoxy)-pyrimidine-2,4-diamine (2.953 g, 9.2 mmol) in 250 mL EtOH and 25 AcOH was added 10% Pd/C. The mixture was placed under 50 psi of H2 via a Parr hydrogenator. After 2.5 h the mixture was filtered through a pad of celite. The pad was washed with ethyl acetate and the solution was partially concentrated in vacuo. The residue was taken up in 500 mL H₂O and cooled to 0° C. The solution was adjusted to pH=12 with 50% NaOH extracted with ethyl acetate. The combined organics were washed with H₂O, washed with brine, dried over Na₂SO₄, filtered and concentrated in vacuo to afford 5-(5-amino-2-Isopropyl-4-methoxy-phenoxy)-pyrimidine-2,4-diamine (2.156 g, 82%) as a dark-orange solid.

Step 2. 1-[5-(2,4-Diamino-pyrimidin-5-yloxy)-4-isopropyl-2-methoxy-phenyl]-3-ethyl-urea

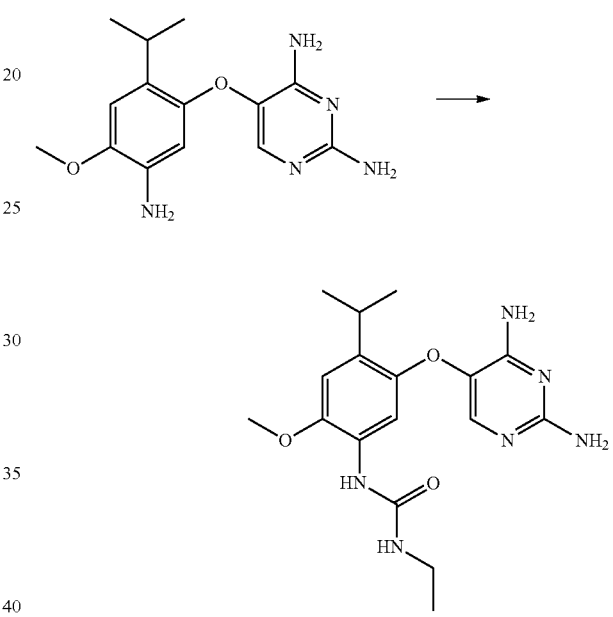

A solution of 5-(5-amino-2-Isopropyl-4-methoxy-phenoxy)-pyrimidine-2,4-diamine (0.117 g, 0.4 mmol) and ethyl isocyanate (0.034 g, 0.5 mmol) in 4 mL of toluene was heated to 100° C. in a sealed tube. After 5 h the solution was cooled and concentrated in vacuo gave a brown solid. Purification via flash chromatography (CH₂Cl₂/MeOH 97:3) afforded 1-[5-(2,4-diamino-pyrimidin-5-yloxy)-4-isopropyl-2-methoxy-phenyl]-3-ethyl-urea (0.120 g, 83%) as a white solid; (M+H)=361.

Example 12. 1-[5-(2,4-diamino-pyrimidin-5-yloxy)-4-isopropyl-2-methoxy-phenyl]-3-phenyl-urea

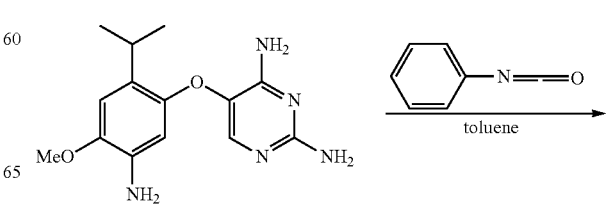

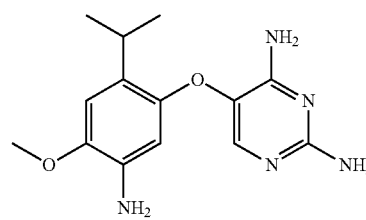

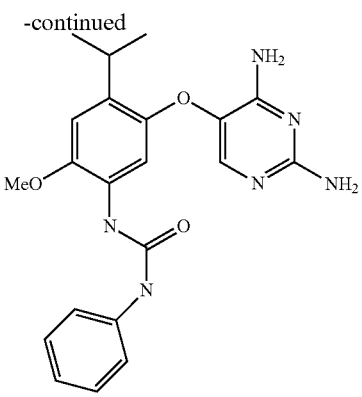

5-(5-amino-2-Isopropyl-4-methoxy-phenoxy)-pyrimidine-2,4-diamine (0.309 g, 1.1 mmol) was converted, as described in the above procedure, to 1-[5-(2,4-diamino-pyrimidin-5-yloxy)-4-isopropyl-2-methoxy-phenyl]-3-phenyl-urea (0.122 g, 28%) as white solid; [MH+]=408.

Similarly prepared from 5-(5-amino-2-Isopropyl-4-methoxy-phenoxy)-pyrimidine-2,4-diamine (0.313 g, 1.1 mmol) and 2,5-hexanedione (0.14 ml, 1.2 mmol) was 5-[5-(2,5-Dimethyl-pyrrol-1-yl)-2-isopropyl-4-methoxy-phenoxy]-pyrimidine-2,4-diamine, (0.259 g, 64%). (M+H)=368.

Example 13. 4-Chloro-N-[5-(2,4-diamino-pyrimidin-5-yloxy)-4-isopropyl-2-methoxy-phenyl]-butyramide

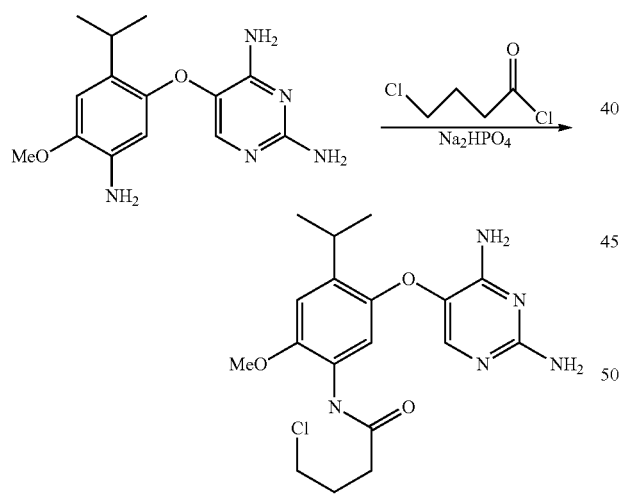

To a solution of 5-(5-amino-2-isopropyl-4-methoxy-phenoxy)-pyrimidine-2,4-diamine (0.400 g, 1.4 mmol) in 15 ml CHCl₃ and Na₂HPO₄ (0.392 g, 2.8 mmol) was added 4-chlorobutyryl chloride (0.194 g, 1.4 mmol) drop-wise. After 4.5 h, H₂O and CH₂Cl₂ were added and the mixture was allowed to stir 15 min. The mixture was neutralized with 2N Na₂CO₃ and extracted with CH₂Cl₂. The combined organics were washed with brine, dried over Na₂SO₄, filtered and concentrated in vacuo to afford 4-chloro-N-[5-(2,4-diamino-pyrimidin-5-yloxy)-4-isopropyl-2-methoxy-phenyl]-butyramide (0.495 g, 91%) as brown foam; [MH]+=394.

Example 14. 5-(2-Isopropyl-5-isothiocyanato-4-methoxy-phenoxy)-pyrimidine-2,4-diamine

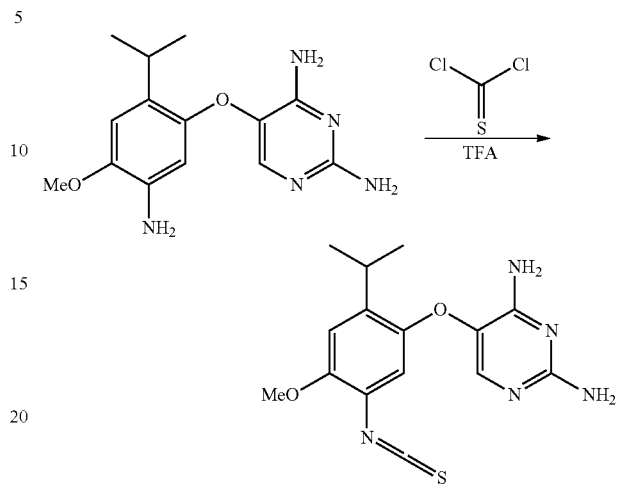

To a solution of 5-(5-amino-2-isopropyl-4-methoxy-phenoxy)-pyrimidine-2,4-diamine (0.100 g, 0.4 mmol) in 1 ml H₂O and TFA (0.040 g, 0.4 mmol) was added thiophosgene (0.040 g, 0.4 mmol). After 1 h the mixture was neutralized with 2M NaOH and extracted with CH₂Cl₂. The combined organics were washed with brine, dried over Na₂SO₄, filtered and concentrated in vacuo to afford 5-(2-isopropyl-5-isothiocyanato-4-methoxy-phenoxy)-pyrimidine-2,4-diamine (0.042 g, 36%) as brown foam [MH]+=334.

Example 15. 2-[5-(2,4-Diaminopyrimidin-5-yloxy)-4-isopropyl-2methoxy-phenyl]-propan-2-ol

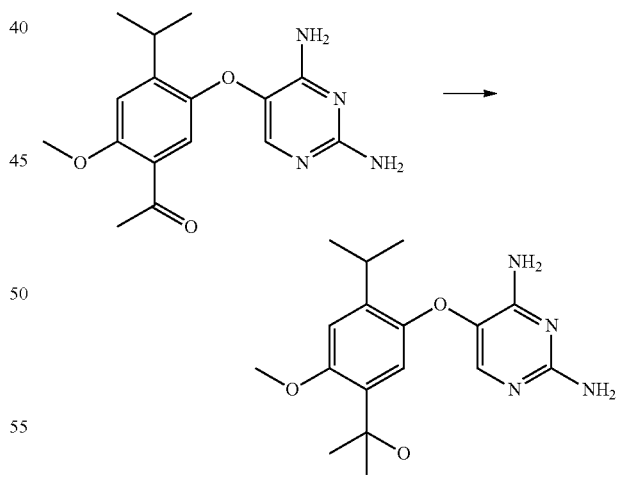

To a solution of methylmagnesium bromide (83.4 mmol, 27.8 ml, 3.0 M in Et₂O) in 83 mL THF at 0° C. was added 1-[5-(2,4-diamino-pyrimidin-5-yloxy)-4-isopropyl-2-methoxy-phenyl]-ethanone (2.523 g, 8.3 mmol, from Example 16) in portions. After 16 h the mixture was cooled to 0° C. and was quenched by the addition 10% NH₄Cl. H₂O was added and the mixture was extracted with ethyl acetate. The combined organics were washed with H₂O, washed with brine, dried over NaHCO₃, filtered and concentrated in vacuo. The crude solid was taken up in 31 ml DMF. K₂CO₃ (0.65 g, 4.7 mmol) and iodomethane (0.098 ml, 1.6 mmol) were added and the mixture was warmed to 50° C. Additional portions of iodomethane (0.019 mL, 0.6 mmol) was added at 1, 2 and 3 hr. After 16 h the mixture was cooled and 10% NH₄Cl and extracted with ethyl acetate. The combined organics were washed with H₂O, washed with brine, dried with Na₂SO₄, filtered and concentrated in vacuo to give 2-[5-(2,4-diaminopyrimidin-5-yloxy)-4-isopropyl-2-methoxy-phenyl]-propan-2-ol (0.711 g, yield) as a white solid. [MH]⁺=333.

Example 16. 5-(2,5-Diiosopropyl-methoxy-phenoxy)-pyrimidine-2,4-diamine

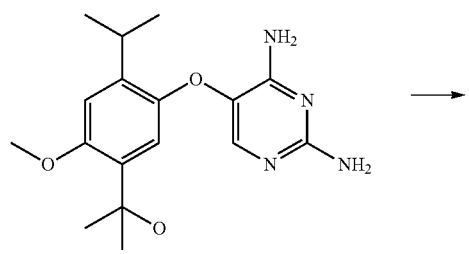

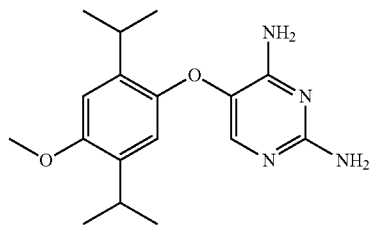

To a solution of 2-[5-(2,4-diaminopyrimidin-5-yloxy)-4-isopropyl-2-methoxy-phenyl]-propan-2-ol: (0.350 g, 1.1 mmol) in 10 ml CH₂Cl₂ was added trifluoroacetic acid (4.0 ml, 52.6 mmol) and triethylsilane (1.7 ml, 10.5 mmol). After 30 min saturated NaHCO₃ was added and the mixture was extracted with ethyl acetate. The combined organics were washed with brine, dried over Na₂SO₄, filtered and concentrated in vacuo to give a crude oil. Purification via flash chromatography (96:4 CH₂Cl₂/MeOH) gave 5-(2,5-diiosopropyl-methoxy-phenoxy)-pyrimidine-2,4-diamine (0.225 g, 68%) as a white solid. [MH]⁺=317.

Example 17. 1-[5-(2,4-Diamino-pyrimidine-5-yloxy)-4-isopropyl-2-methoxy-phenyl]-ethanol

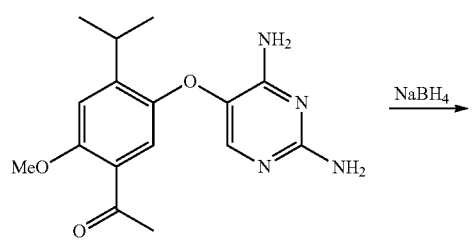

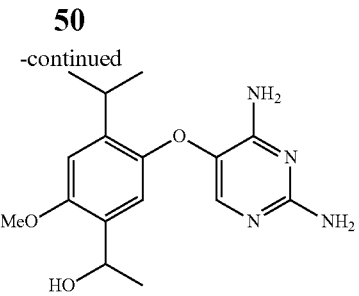

To a solution of 1-[5-(2,4-diamino-pyrimidin-5-yloxy)-4-isopropyl-2-methoxy-phenyl]-ethanone (2.500 g, 8.3 mmol) in 100 ml MeOH was slowly added NaBH₄ (1.566 g, 41.4 mmol) at 0° C. The solution was allowed to warm to rt. After 20 h, the saturated NH₄Cl was added, the mixture was concentrated in vacuo and extracted with ethyl acetate. The combined organics were washed with brine, dried over Na₂SO₄, filtered and concentrated in vacuo. Purification via silica gel column chromatography (9:1 CH₂Cl₂/MeOH) afforded to 1-[5-(2,4-diamino-pyrimidine-5-yloxy)-4-isopropyl-2-methoxy-phenyl]-ethanol (1.613 g, 60%) as white foam; [MH]⁺=301.

Example 18. 5-(2-Isopropyl-4-methoxy-5-vinyl-phenoxy)-pyrimidine-2,4-diamine and 5-[2-Isopropyl-4-methoxy-5-(1-methoxy-ethyl)-phenoxy]-pyrimidine-2,4-diamine

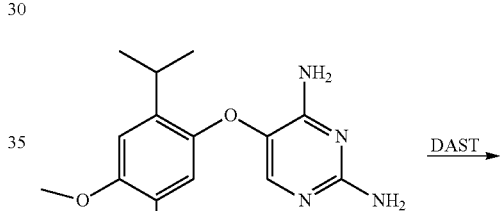

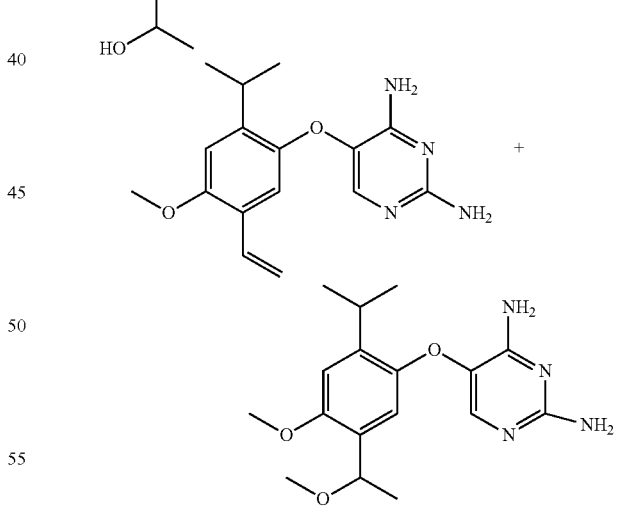

To a solution of 1-[5-(2,4-Diamino-pyrimidin-5-yloxy)-4-isopropyl-2-methoxy-phenyl]-ethanol (1.613 g, 5.3 mmol) in 30 ml CH₂Cl₂ at −78° C. was added DAST (0.935 g, 5.8 mmol). After stirring 1.5 h, saturated NaHCO₃ was added and the mixture was extracted by CH₂Cl₂. The combined organics were washed with brine and dried with Na₂SO₄, filtered and concentrated in vacuo. Purification via silica gel chromatography (95:5 CH₂Cl₂/MeOH) gave 5-(2-Isopropyl-4-methoxy-5-vinyl-phenoxy)-pyrimidine-2,4-diamine (0.044 g, 3%) as a foam ([MH]⁺=301) and 5-[2-Isopropyl-4-methoxy-5-(1-methoxy-ethyl)-phenoxy]-pyrimidine-2,4-diamine (0.075 g, 4%) as foam. [MH]⁺=303.

Example 19. 5-(2,4-Diamino-pyrimidin-5-yloxy)-4-isopropyl-2-methoxy-N-methyl-benzenemethylsulfonamide Step 1. 5-(2,4-Diamino-pyrimidin-5-yloxy)-4-isopropyl-2-methoxy-benzenesulfonyl Chloride

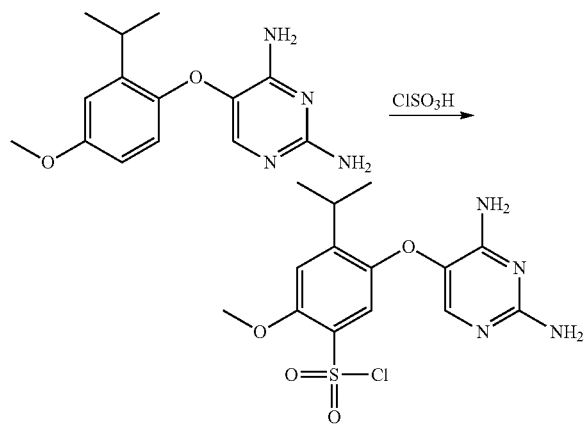

A mixture of pyrimidine (0.400 g, 1.5 mmol) in 2 ml chlorosulfonic acid was allowed to stir 20 min. The mixture was poured over ice. The precipitate was filtered, washed by cold H₂O and dried under vacuum to afford 5-(2,4-diamino-pyrimidin-5-yloxy)-4-isopropyl-2-methoxy-benzenesulfonyl chloride (0.515 g, 95%) as a white solid; [MH]⁺=373.

Step 2. 5-(2,4-Diamino-pyrimidin-5-yloxy)-4-isopropyl-2-methoxy-N-methyl-benzenemethylsulfonamide

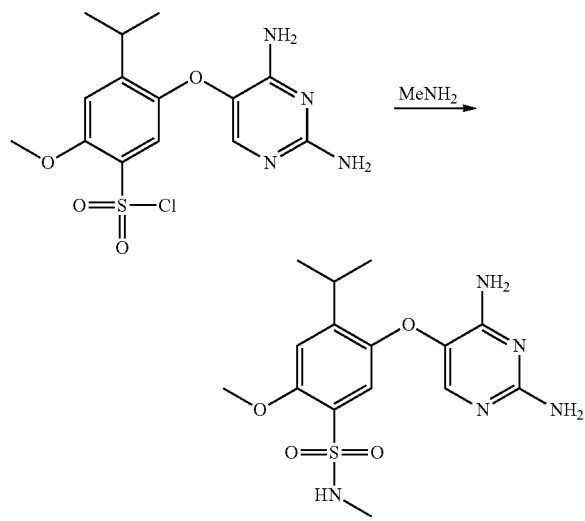

To 10 ml methyl amine −78° C. in a screw-capped tube was added 5-(2,4-diamino-pyrimidin-5-yloxy)-4-isopropyl-2-methoxy-benzenesulfonyl chloride (0.300 g, 0.8 mmol).

The mixture was allowed to warm to room temperature. After 20 hours the mixture was evaporated, washed with H₂O, and dried under vacuum to afford 5-(2,4-diamino-pyrimidin-5-yloxy)-4-idopropyl-2-methoxy-N-methyl-benzenemethylsulfonamide (0.170 g, 57%) as a white solid; mp (HCl salt)=252.3-252.9° C.; [MH]⁺=367.

Similarly prepared, replacing methylamine with ethylamine, was 5-(2,4-Diamino-pyrimidin-5-yloxy)-N-ethyl-4-isopropyl-2-methoxy-benzenesulsonamide (0.186 g, 61%) as a white solid; mp (HCl salt)=260-265° C.; [MH]⁺=382.

Example 20. 5-(2,4-Diamino-pyrimidin-5-yloxy)4-isopropyl-2-methoxy-N,N-dimethyl-benzamide

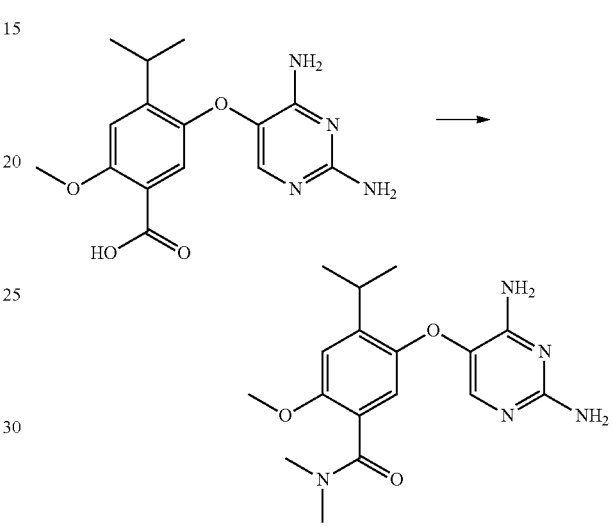

To a suspension of 5-(2,4-Diamino-pyrimidin-5-yloxy)-4-isopropyl-2-methoxy-benzoic acid (180 mg, 0.57 mmol, from Example 17) in anhydrous dichloromethane (5.6 mL) was added trifluoroacetic acid (0.08 mL, 1.14 mmol) and then thionyl chloride (0.36 mL, 5.65 mmol). After 1 hour the reaction was concentrated. To the residue was added anhydrous dichloromethane (4.5 mL) and dimethylamine (2.84 mL of a 2M solution in tetrahydrofuran, 5.65 mmol). After 2 hours stirring at room temperature, the reaction was filtered and concentrated. Purification via silica gel column chromatography eluting with 95/5/0.1 to 93/7/0.1 dichloromethane/methanol/ammonium hydroxide yielded 5-(2,4-diamino-pyrimidin-5-yloxy)4-isopropyl-2-methoxy-N,N-dimethyl-benzamide (40 mg, 20%) as pale yellow solid, MS (M+H)=346.

Similarly prepared using methylamine instead of dimethylamine, 5-(2,4-diamino-pyrimidin-5-yloxy)-4-isopropyl-2-methoxy-N-methyl-benzamide (23 mg, 15%) was prepared as pale yellow solid, MS (M+H)=332.

Example 21. 4-(2,4-Diamino-pyrimidin-5-yloxy)-2-iodo-5-isopropyl-phenol

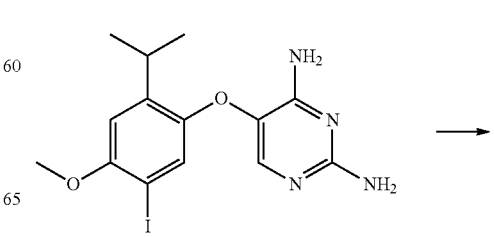

-continued

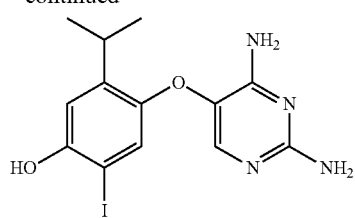

To a cold suspension of 1 (0.21 g, 0.52 mmol) in dichloromethane (15 ml) at 0° C. was added BBr₃ (0.26 g, 1.05 mmol). The reaction mixture was stirred at room temperature for 16 hrs., quenched with water and basified with sat. NaHCO₃. The insoluble solid was collected by filtration. The filtrate was washed with water, dried over Na₂SO₄, filtered and concentrated in vacuo. The combined residue was purified via flash chromatographed on silica gel (3 to 5% methanol in dichloromethane with 0.1% NH₄OH) gave desired product (0.174 g, 86%), (M+H)=387.

Example 22. 5-(5-Iodo-2-isopropyl-4-prop-2-ynyloxy-phenoxy)-pyrimidine-2,4-diamine

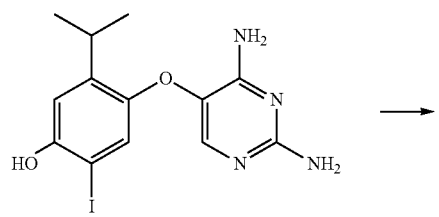

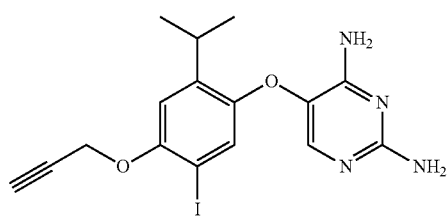

To 4-(2,4-Diamino-pyrimidin-5-yloxy)-2-iodo-5-isopropyl-phenol (200 mg, 0.43 mmol) dissolved in anhydrous N,N-dimethylformamide (2 mL) was added anhydrous potassium carbonate (414 mg, 3.00 mmol) and propargyl chloride (0.03 mL, 0.43 mmol). After stirring at room temperature overnight, the reaction was extracted with dichloromethane, water and brine. The dichloromethane layer was dried using anhydrous magnesium sulfate, concentrated, and purified via silica gel column chromatography (95/5/0.1 dichloromethane/methanol/ammonium hydroxide) to yield 5-(5-iodo-2-isopropyl-4-prop-2-ynyloxy-phenoxy)-pyrimidine-2,4-diamine as white solid (131 mg, 71%), MS (M+H)=425.

Example 23. 5-(5-Ethanesulfonyl-2-isopropyl-4-methoxyphenoxy)-pyrimidine-2,4-diamine

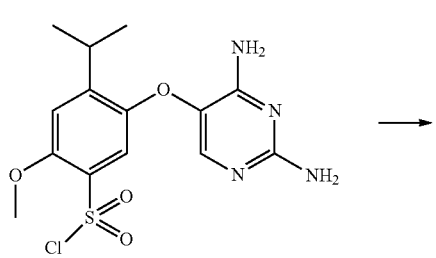

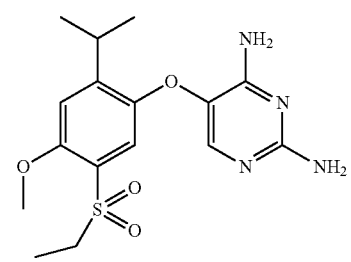

To a solution of sodium sulfite (541 mg, 4.29 mmol) in water (20 mL) was added 5-(2,4-Diamino-pyrimidin-5-yloxy)-4-isopropyl-2-methoxy-benzenesulfonyl chloride (400 mg, 1.07 mmol) and the reaction was heated at 80° C. for 1 hour. Sodium bicarbonate (361 mg, 4.29 mmol-dissolved in 5 mL water), dioxane (20 mL), and ethyl iodide (0.10 mL, 1.29 mmol) were added and the reaction was heated at 80° C. for 2 hours. The reaction was concentrated, extracted with dichloromethane (150 mL) and water (20 mL). The dichloromethane layer was dried using anhydrous sodium sulfate, concentrated, and purified via silica gel column chromatography (95/5/0.1 dichloromethane/methanol/ammonium hydroxide) to yield 5-(5-ethanesulfonyl-2-isopropyl-4-methoxy-phenoxy)-pyrimidine-2,4-diamine (77 mg, 20%) as white solid, MS (M+H)=367.

Example 24. 5-(2-Isopropyl-4-methoxy-5-trifluoromethyl-phenoxy)-pyrimidine-2,4-diamine The synthetic procedure used in this Example is outlined in Scheme E.

SCHEME E

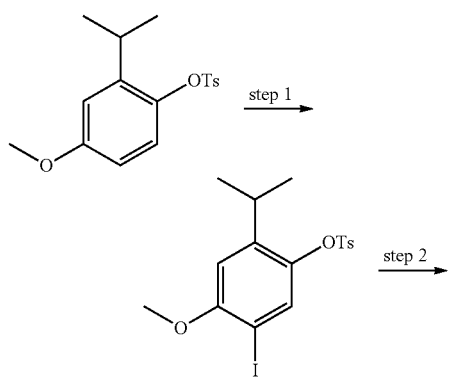

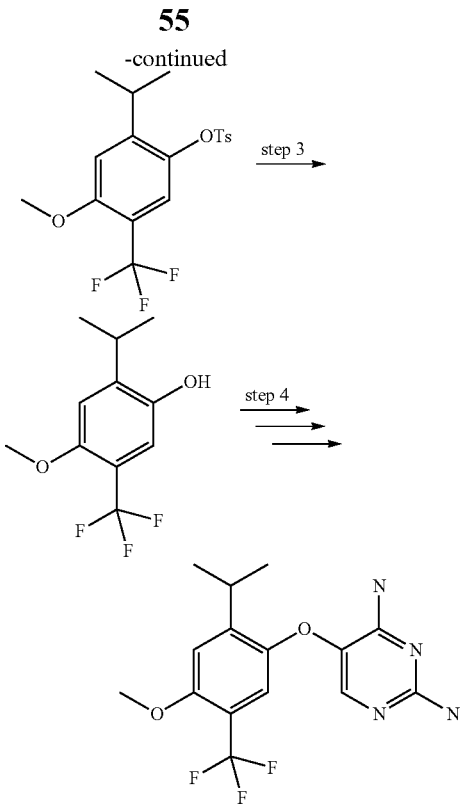

Step 1. 1-Iodo-4-isopropyl-2-methoxy-5-(toluene-4-sulfonyl)-benzene

To a solution of 2-Isopropyl-4-methoxy-1-(toluene-4-sulfonyl)-benzene (10 g, 31.25 mmol) in HOAc (10 ml) was added a solution of ICl (9.6 g, 59.26 mmol) in HOAc (10 ml) and $H_2O$ (5 ml). The reaction mixture was stirred at room temperature for 16 hrs and basified by saturated $NaHCO_3$ solution. The aqueous solution was extracted into EtOAc which was washed with water, brine, dried over $Na_2SO_4$, filtered and concentrated in vacuo to give 1-Iodo-4-isopropyl-2-methoxy-5-(toluene-4-sulfonyl)-benzene (12.35 g, 89%).

Step 2. 1-Isopropyl-5-methoxy-2-(toluene-4-sulfonyl)-4-trifluoromethyl-benzene To a hot mixture of 1-Iodo-4-isopropyl-2-methoxy-5-(toluene-4-sulfonyl)-benzene (0.5 g, 1.12 mmol), CuI, KF in anhydrous DMF (10 ml) at 120° C. oil bath temperature, was added trifluoromethyl iodide (0.64 g, 4.48 mmol) in portions over 30 min. The reaction mixture was heated for 4 hrs and poured into $H_2O$ (100 ml). The insoluble solid, which was collected by filtration, was triturated with methylene chloride, filtered and concentrated to give 1-Isopropyl-5-methoxy-2-(toluene-4-sulfonyl)-4-trifluoromethyl-benzene (0.45 g, 100%) as a solid.

Step 3. 2-Isopropyl-4-methoxy-5-trifluoromethyl-phenol

A solution of 1-Isopropyl-5-methoxy-2-(toluene-4-sulfonyl)-4-trifluoromethyl-benzene (0.40 g, 1.03 mmol) and NaOH (0.5 g, 12.5 mmol) in MeOH (5 ml) and $H_2O$ (5 ml) was heated at 90° C. for 2 hrs. The cooled reaction mixture was acidified with 3N HCl and extracted into methylene chloride. The combined extracts was dried with $Na_2SO_4$, filtered and concentrated to give desired 2-Isopropyl-4-methoxy-5-trifluoromethyl-phenol (0.194 g, 81%) as an oil.

Step 4. 5-(2-Isopropyl-4-methoxy-5-trifluoromethyl-phenoxy)-pyrimidine-2,4-diamine Following the procedure of Example 2 steps 5-7, 2-Isopropyl-4-methoxy-5-trifluoromethyl-phenol was converted to 5-(2-Isopropyl-4-methoxy-5-trifluoromethyl-phenoxy)-pyrimidine-2,4-diamine. (M+H)=343.

Example 25. 5-(2,4-Diamino-pyrimidin-5-yloxy)-4-isopropyl-2-methoxy-thiobenzamide

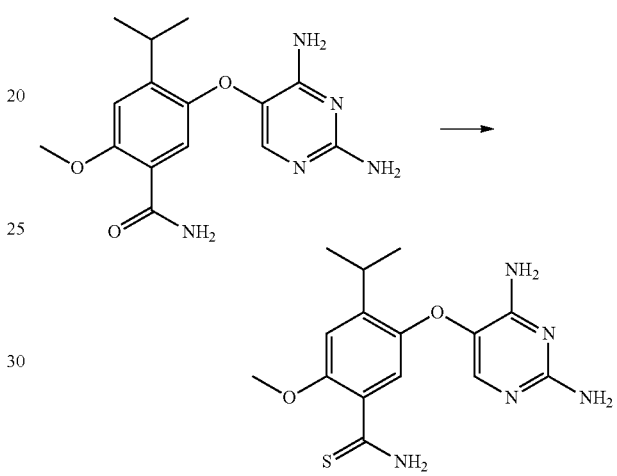

A mixture of 5-(2,4-Diamino-pyrimidin-5-yloxy)-4-isopropyl-2-methoxy-benzamide (0.25 g, 0.79 mmol, prepared according to the procedure of Example 52) and Lawesson's reagent (0.96 g, 2.37 mmol) in anhydrous THF (20 ml) was stirred at room temperature for 16 hrs and concentrated in vacuo. Flash chromatography on silica (5% $CH_3OH$ in methylene chloride with 1% $NH_4OH$) gave 5-(2,4-Diamino-pyrimidin-5-yloxy)-4-isopropyl-2-methoxy-thiobenzamide (0.201 g, 76%) as a yellow solid.

Example 26. 5-(4-Ethoxy-5-iodo-2-isopropyl-phenoxy)-pyrimidine-2,4-diamine

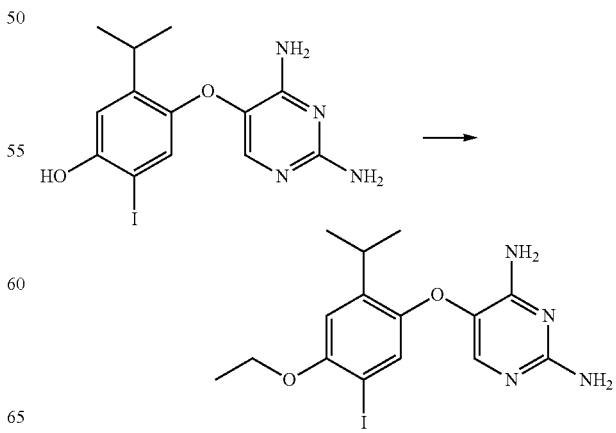

To a solution of 4-(2,4-Diamino-pyrimidin-5-yloxy)-2-iodo-5-isopropyl-phenol (0.2 g, 0.52 mmol) in anhydrous DMF (2 ml) was added EtBr (57 mg, 0.52 mmol) in portions. The reaction mixture was partitioned between EtOAc and $H_2O$. The organic extract was dried over $Na_2SO_4$, filtered and concentrated. Flash chromatography on silica (3% MeOH in methylene chloride with 1% $NH_4OH$) gave 5-(4-Ethoxy-5-iodo-2-isopropyl-phenoxy)-pyrimidine-2,4-diamine (0.17 g, 28%) as a yellow solid. (M+H)=415.

Example 27. Formulations

Pharmaceutical preparations for delivery by various routes are formulated as shown in the following Tables. "Active ingredient" or "Active compound" as used in the Tables means one or more of the Compounds of Formula (I).

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Compound 16 Tablets

Compound 16 is supplied formulated in a film-coated tablet containing 10, 20, 30, 50, 100 or 300 mg of Compound 16. Tablets are formulated with USP/NF compendial grade lactose monohydrate, hydroxypropyl methyl cellulose (HPMC or Hypromellose), croscarmellose sodium, microcrystalline cellulose (Avicel PH102), and magnesium stearate as described in Table 2. Tablets are film-coated with Opadry Yellow (Colorcon, Inc.) and packaged in HDPE bottles with child resistant caps and induction seals.

TABLE 2

Compound 16: Quantitative Tablet Composition (300 mg and Placebo)

| Component | Grade | Function | Amount for 300 mg Tablet (mg) | Amount for Placebo Tablet (mg) |
| --- | --- | --- | --- | --- |
| Intragranular | | | | |
| Compound 16 (milled) | In house | Active | 300.0 | 0 |
| Lactose monohydrate | USP/NF | Diluent | 187.8 | 487.8 |
| Croscarmellose sodium | USP/NF | Disintegrant | 18.0 | 18.0 |
| Hydroxypropyl methyl cellulose | USP/NF | Binder | 18.0 | 18.0 |
| Extragranular | | | | |
| Croscarmellose sodium | USP/NF | Disintegrant | 12.0 | 12.0 |

TABLE 2-continued

Compound 16: Quantitative Tablet Composition (300 mg and Placebo)

| Component | Grade | Function | Amount for 300 mg Tablet (mg) | Amount for Placebo Tablet (mg) |
|---|---|---|---|---|
| Microcrystalline Cellulose | USP/NF | Diluent | 60.0 | 60.0 |
| Magnesium Stearate | USP/NF | Lubricant | 4.2 | 4.2 |
| Core Tablet | | | 600 | 600 |
| Film Coating | | | | |
| Opadry Yellow 03K12429 | * | Film-coat | 18.0 | 18.0 |
| Sterile Water for Irrigation | USP/NF | Granulating Solution | As needed | As needed |
| Total Weight of Film Coated Tablet | | | 618 | 618 |

*: Opadry Yellow is composed of the following USP/NF excipients: hypromellose, titanium dioxide, talc, triacetin and yellow iron oxide.

Example 28. P2X3/P2X2/3 FLIPR (Fluorometric Imaging Plate Reader) Assay

CHO-K1 cells were transfected with cloned rat P2X3 or human P2X2/3 receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final concentration]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well agonist or vehicle addition. The agonist was a 2X solution of α,β-meATP producing a final concentration of 1 µM (P2X3) or 5 µM (P2X2/3). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the present disclosure exhibited activity for the P2X3 receptor. The compound 4-(2,4-Diamino-pyrimidin-5-yloxy)-2-iodo-5-isopropyl-phenol, for example, exhibited a $pIC_{50}$ of approximately 8.3 using the above assay.

Example 29. In Vivo Assay for Cough Sensitization

Hartley guinea pigs are studied in a standard tussive protocol. Briefly, guinea pigs (N=4-8/group) are treated with inhalation of nebulized citric acid following prior sensitization with inhaled histamine or alpha, beta-methylene ATP, and monitored for the development of coughing nots, as observed by an experienced investigator. Animals receive vehicle (p.o. or by nebulized inhalation) or a compound of the present disclosure (from 1 to 100 mg/kg p.o., or at increasing nebulized concentrations), 30-60 minutes prior to the inhalational challenge of histamine or alpha, beta-methylene ATP, followed by citric acid solution.

Cough responsiveness is then monitored by counting frequency following challenge provocation, such that the magnitude by which a compound as described herein inhibits the frequency of tussive response can be calculated.

Example 30. Inhibition of ATP-Gated P2X3 Channels by Compound 16: an Effective Anti-Tussive Mechanism in Chronic Cough Evidence suggests that P2X3 receptors are expressed by airway vagal afferents and contribute to the hyperexcitability of sensory neurons. Thus, the inventors explored the role of P2X3 receptors in the sensitization of vagal pathways mediating the cough reflex leading to chronic cough (CC). A study was performed to investigate the efficacy of oral administration of Compound 16 in reducing daytime cough in idiopathic/treatment-resistant chronic cough.

In this study, a double-blind randomized placebo-controlled crossover trial, 24 subjects (19 women, mean age 55 yrs) were randomized into a double blind, placebo-controlled, 2-period, crossover study, of Compound 16, 600 mg bd. Cough was assessed using an ambulatory sound monitoring system at baseline and after 2 weeks of treatment; primary endpoint, daytime objective cough frequency (coughs/hr) (VitaloJAK™); secondary endpoints, cough severity and urge to cough (UTC) visual analogue scales (VAS), global ratings of change and cough quality of life questionnaire (CQLQ).

Compound 16 markedly reduced cough (mean difference vs. placebo): daytime coughs/hr −75% (95% CI −50 to −88), $p<0.001$ (FIG. 1); cough severity VAS −26 mm (−10 to −42), $p=0.003$; UTC VAS −21 mm (−2 to −41), $p=0.035$; and CQLQ −9 (−2 to −17), $p=0.018$. 13/24 of Compound 16 patients rated an improved cough compared to 2/22 treated with placebo. Therefore, Compound 16 demonstrated substantial anti-tussive effects relative to placebo. In fact, treatment with Compound 16 surprisingly produced a 75% reduction in objective daytime cough counts, in patients with refractory chronic cough.

Example 31

Compound 16 has progressed to completion of 6 Phase 1 studies and 5 Phase 2 studies, with several studies in progress or soon to commence, and over 400 subjects dosed at least once with Compound 16. Clinical safety so far has been excellent, and AEs associated with Compound 16 in patients and healthy volunteers are limited to oropharyngeal findings (hypogeusia) arising from dose-dependent attenuation of gustatory afferent transmission, likely mediated by P2X2/3 heterotrimer inhibition, notable at higher dose levels used so far. Studies in normal healthy volunteers have explored safety, tolerability and pharmacokinetics of Compound 16 following oral administration of doses from 10 mg to 1800 mg for up to 3 weeks. All repeated dose studies have been undertaken with a simple immediate release (IR) oral formulation, and oral bioavailability appears to be high, based on % dose recovered in urine. Plasma half-life falls in the range of 7-9 h, with steady state for BID dosing achieved after 3 doses.

Patient studies completed to date include a single-center proof concept efficacy study of Compound 16 (600 mg BID, 14 d) in chronic cough; a multi-center proof of concept efficacy study of Compound 16 (300 mg BID, 28 d) in painful osteoarthritis (OA) of the knee; and a multi-center proof of concept efficacy study of Compound 16 (50-300 mg BID, dose titration, 28 d) in bladder pain syndrome (BPS). In addition, one exploratory challenge study has been undertaken in mild asthmatic patients with established bronchial hyperreactivity, in which the effect of steady state exposure following doses of Compound 16 of 50 mg and 300 mg were examined on bronchospasm (expressed as PC20) to inhaled doubling doses of ATP and methacholine. Most recently, a multicenter dose-escalation (P2b) study in chronic cough has been completed, utilizing dose levels of 50, 100, 150 and 200 mg BID versus placebo, with objective cough monitoring at each dose level.

Example 32

In a study with 29 randomized chronic cough patients employing doses of 50 mg, 100 mg, 150 mg and 200 mg twice daily for 4 days, a significant reduction in cough frequency was demonstrated, including at the lowest dose of 50 mg twice daily. Cough frequency was measured objectively utilizing a cough recording device, with periodic measurements following Compound 16 treatment compared to a baseline recording.

All Compound 16 doses, including the lowest dose of 50 mg twice daily, demonstrated a statistically significant reduction in awake cough frequency compared to placebo ($p \leq 0.002$).

Compound 16 was generally well tolerated. The incidence of decreased taste acuity, as observed in the first study at 600 mg twice daily, was much less at the 50 mg dose. Only one patient discontinued treatment at any dose in the current study, due to the taste effect.

The 29-patient randomized, double-blind, placebo controlled, Phase 2b crossover study was conducted at 10 clinical sites in the U.S. Patients were randomized to either Compound 16 or placebo arms. Those in the treatment group received Compound 16 50 mg, followed by a titration up to 100 mg, 150 mg and 200 mg, with each dose given twice daily for four days. Treatment period one was followed by a 3-5 day washout period. Patients were then crossed over to the alternate arm of the study and treated with either Compound 16 or placebo for 16 more days.

Figure 2:
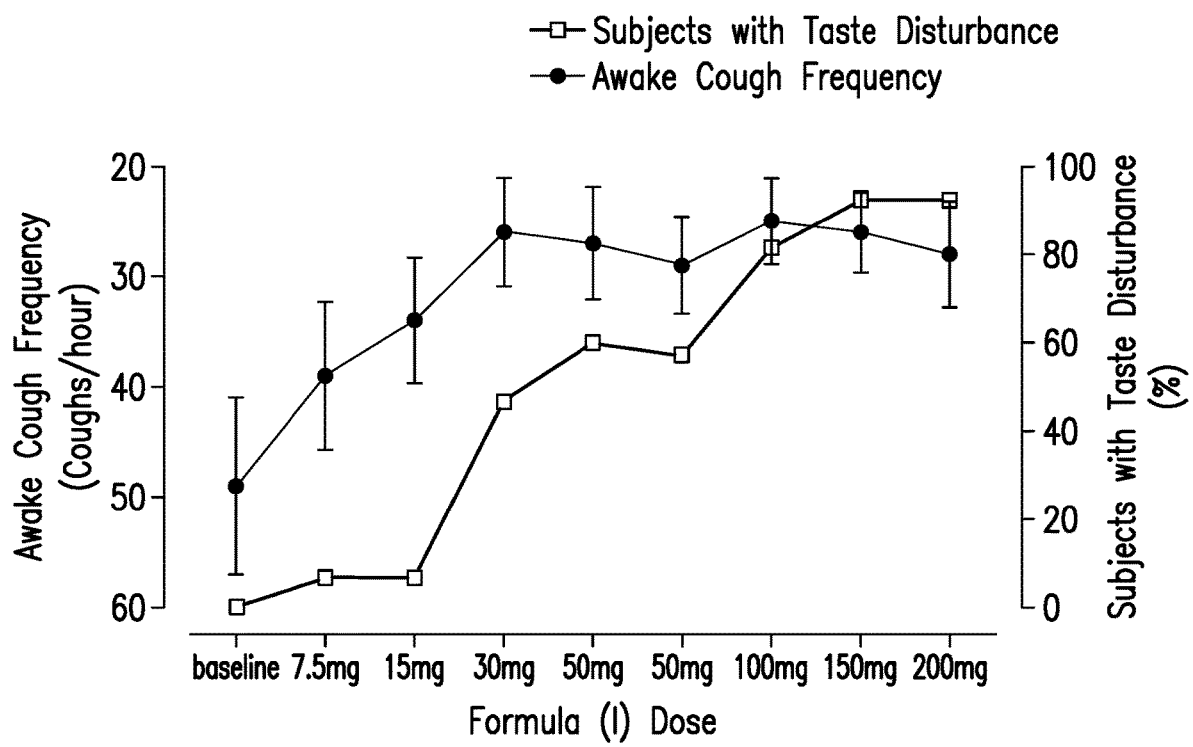
FIG. 2 illustrates the separation between the effect on cough relative to the effect on taste which is achieved with doses of the compound of Formula (I) of less than approximately 7.5 mg twice daily, 7.5 mg twice daily to approximately 15 mg twice daily, approximately 15 mg twice daily to approximately 30 mg twice daily, or approximately 30 mg twice daily to approximately 50 mg twice daily.

In studies with even lower doses of the compound of Formula (I), an effective separation between an effect on cough and an effect on taste is observed; such separation can be achieved with doses of less than approximately 7.5 mg twice daily, 7.5 mg twice daily to approximately 15 mg twice daily, approximately 15 mg twice daily to approximately 30 mg twice daily, or approximately 30 mg twice daily to approximately 50 mg twice daily (see FIG. 2).

Figure 3:
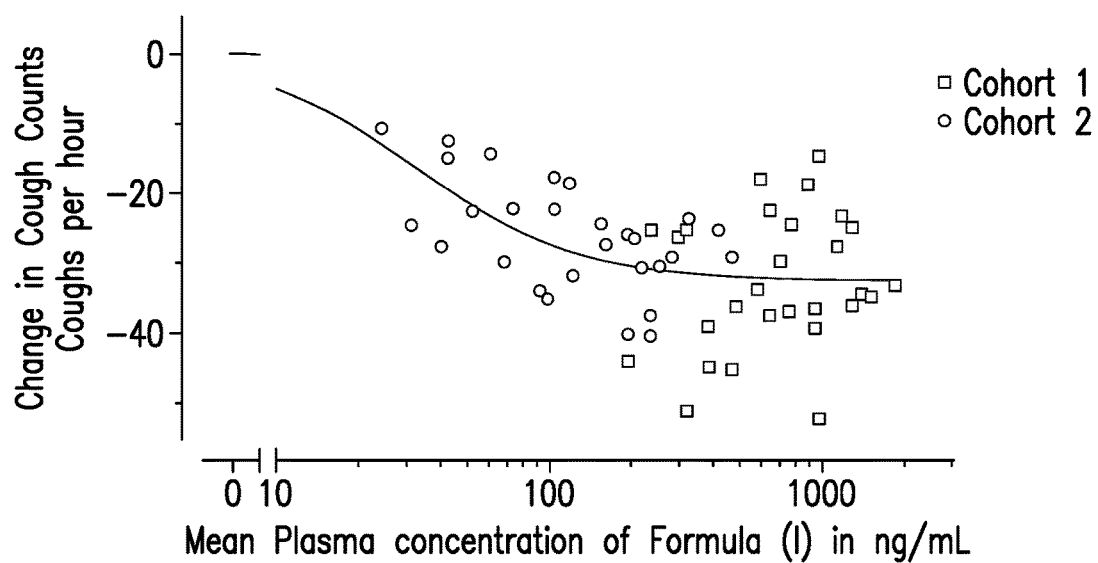
FIG. 3 correlates the concentration of Formula (I) in plasma with the effect thereof on cough.

When patients with chronic cough are given a compound of Formula (I), the concentrations of Formula (I) in plasma are seen to be correlated with their effect on cough. For example, an effective treatment of cough can be achieved by a concentration of less than approximately 20 ng/mL; in certain embodiments, an effective treatment of cough can be achieved by a concentration between approximately 20 ng/mL and approximately 50 ng/mL; in certain embodiments, an effective treatment of cough can be achieved by a concentration between approximately 50-100 ng/mL; in certain embodiments, an effective treatment of cough can be achieved by a concentration between approximately 100-200 ng/mL; in certain embodiments, an effective treatment of cough can be achieved by a concentration between approximately 200-400 ng/mL; in certain embodiments, an effective treatment of cough can be achieved by a concentration between approximately 400-1000 ng/mL (see FIG. 3).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for treating chronic cough, comprising administering to a patient with chronic cough from about 30 mg to about 50 mg twice daily of a compound of Formula (I):

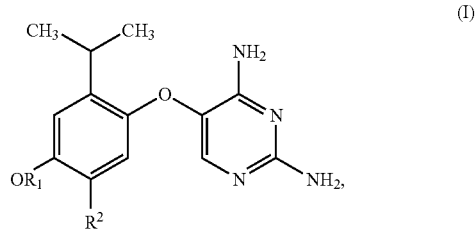

or a pharmaceutically acceptable salt thereof, wherein:
$R^1$ is hydrogen or $C_1$-$C_6$ alkyl; and
$R^2$ is: alkyl; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl; and
wherein the method exhibits a reduced taste disturbance relative to a taste disturbance resulting from administering a dose of about 100 mg or greater of the compound of formula (I), or the pharmaceutically acceptable salt thereof, twice daily to a patient with chronic cough.

2. The method of claim 1, wherein the chronic cough is idiopathic or treatment resistant cough.

3. The method of claim 1, wherein the compound of Formula (I), or the pharmaceutically acceptable salt thereof, is administered twice daily for days, weeks, months or years.

4. The method of claim 1, wherein the chronic cough is refractory chronic cough.

5. The method of claim 1, wherein the reduced taste disturbance is relative to a taste disturbance resulting from administering about 100 mg of the compound of Formula (I), or the pharmaceutically acceptable salt thereof, twice daily to a patient with chronic cough.

6. The method of claim 1, wherein the chronic cough is daytime cough.

7. The method of claim 1, wherein the compound is selected from:

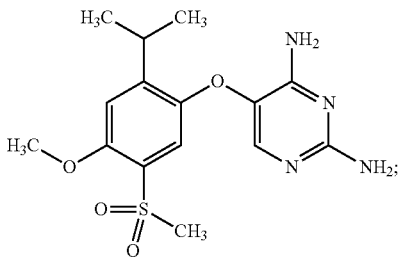

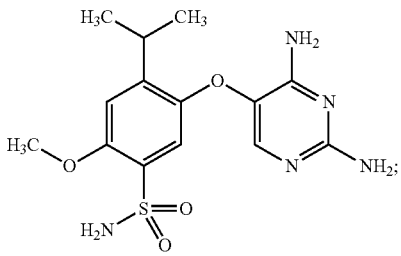 [SMILES: COc1cc(C(C)C)c(Oc2cnc(N)nc2N)cc1S(N)(=O)=O]

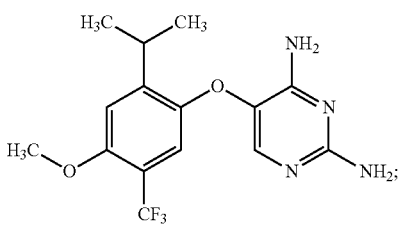

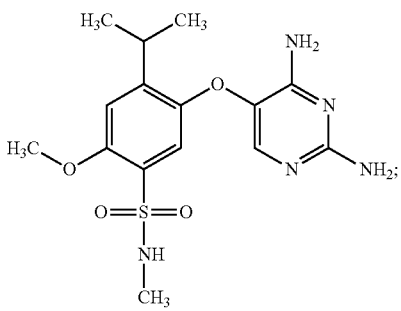

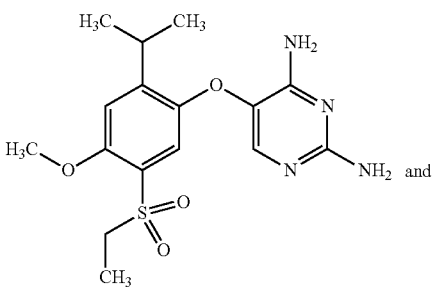 and

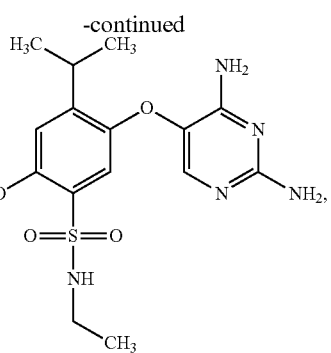

or a pharmaceutically acceptable salt thereof.

8. The method of claim 1, wherein the compound is

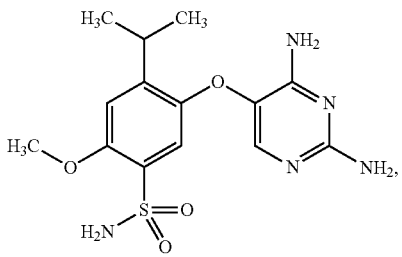 [SMILES: COc1cc(C(C)C)c(Oc2cnc(N)nc2N)cc1S(N)(=O)=O]

or a pharmaceutically acceptable salt thereof.

9. A method for treating chronic cough, comprising administering to a patient with chronic cough from about 30 mg to about 50 mg twice daily of a pharmaceutically acceptable salt of the following compound:

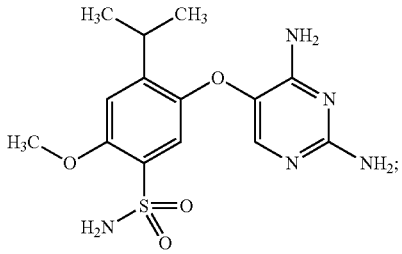

wherein the method exhibits a reduced taste disturbance relative to a taste disturbance resulting from administering a dose of about 100 mg or greater of the pharmaceutically acceptable salt of the compound of formula (I) twice daily to a patient with chronic cough.

10. The method of claim 9, wherein the reduced taste disturbance is relative to a taste disturbance resulting from administering about 100 mg of the pharmaceutically acceptable salt of the compound of formula (I) twice daily to a patient with chronic cough.

11. The method of claim 9, wherein the reduced taste disturbance is relative to a taste disturbance resulting from administering about 600 mg of the pharmaceutically acceptable salt of the compound of formula (I) twice daily to a patient with chronic cough.

* * * * *